US008557533B2

(12) United States Patent
Schneider et al.

(10) Patent No.: US 8,557,533 B2
(45) Date of Patent: Oct. 15, 2013

(54) SCREENING METHOD FOR THE IDENTIFICATION OF AGENTS CAPABLE OF ACTIVATING CD4+CD25+ REGULATORY T-CELLS THROUGH INTERACTIONS WITH THE HIV-1 GP120 BINDING SITE ON CD4

(75) Inventors: Franz-Josef Schneider, Laupheim (DE); Christian Becker, Mainz (DE); Tobias Bopp, Aabergen (DE); Helmut Jonuleit, Ginsheim-Gustavsburg (DE); Edgar Schmitt, Mainz (DE)

(73) Assignee: Helmut Jonuleit (DE)

( * ) Notice: Subject to any disclaimer, the term of this patent is extended or adjusted under 35 U.S.C. 154(b) by 716 days.

(21) Appl. No.: 12/525,142

(22) PCT Filed: Jan. 30, 2008

(86) PCT No.: PCT/EP2008/051144

§ 371 (c)(1),
(2), (4) Date: Oct. 7, 2009

(87) PCT Pub. No.: WO2008/092905

PCT Pub. Date: Aug. 7, 2008

(65) Prior Publication Data

US 2010/0074904 A1 Mar. 25, 2010

(30) Foreign Application Priority Data

Feb. 1, 2007 (EP) .................................... 07101604
Dec. 5, 2007 (EP) .................................... 07122424

(51) Int. Cl.
*G01N 33/00* (2006.01)
*C12Q 1/00* (2006.01)
*C12N 5/071* (2010.01)
*A61K 39/21* (2006.01)

(52) U.S. Cl.
USPC ......... 435/7.24; 435/5; 435/372.3; 424/208.1

(58) Field of Classification Search
None
See application file for complete search history.

(56) References Cited

U.S. PATENT DOCUMENTS 4,695,459 A 9/1987 Steinman et al.
6,455,497 B1 9/2002 Goronzy et al.
2005/0048587 A1 3/2005 Rao et al.

FOREIGN PATENT DOCUMENTS

JP 2-152989 A 2/1990
WO 2004/083247 A1 9/2004
WO 2007/035551 A1 3/2007

OTHER PUBLICATIONS

Stassen, M., et al., 2004, Human CD25+ regulatory T cells: two subsets defined by the integrins alpha4beta7 or alpha4beta1 confer distinct suppressive properties upon CD4+ T helper cells, Eur. J. Immunol. 34:1303-1311.*

Bopp, T., et al., 2007, Cyclic adenosine monophosphate is a key component of regulatory T cell-mediated suppression, J. Exp. Med. 204(6):1303-1310.*

Becker, C., et al., 2007, CD4-mediated functional activation of human CD4+CD25+ regulatory T cells, Eur. J. Immunol. 37:1217-1223.*

Larkin, J., et al., 2007, Activation of CD4+CD25+ regulatory T cell suppressor function by analogs of the selecting peptide, Eur. J. Immunol. 37:139-146.*

Bopp, Tobias., et al; Cyclic Adenosine Monophosphate is a Key Component of regulatory T Cell-Mediated Suppression; JEM (2007) vol. 204, No. 6 pp. 1303-1310.

International Search Report for PCT/EP2008/051144 mailed on Aug. 27, 2008.

Larkin, Joseph., et al; Activation of CD4+CD25+ Regulatory T Cell Suppressor Function by Analogs of the Selecting Peptide; Eur. Journal Immunology (2007) vol. 37 pp. 139-146.

Mizukami, Tamio., et al; Binding Region for Human Immunodeficiency Virus (HIV) and Epitopes for HIV-Blocking Monoclonal Antibodies of the CD4 Molecule Defined by site-directed Mutagenesis; Proc. Natl. Acad. Science. USA (1988) vol. 85 pp. 9273-9277.

Nilsson, Jakob., et al; HIV-1—Driven regulatory t-Cell Accumulation in Lymphoid Tissues is Associated with Disease Progression in HIV/AIDS; Blood (2006) vol. 108, No. 12 pp. 3808-3817.

Vendetti, Silvia., et al; Human CD4+ T Lymphocytes with Increased intracellular cAMP Levels Exert Regulatory Functions by Releasing Extracellular cAMP; Journal of Leukocyte Biology (2006) vol. 80, No. 4 pp. 880-888.

Watanabe, Tomoko., et al; CD52 is a Novel Costimulatory Molecule for Induction of $CD4^+$ Regulatory T Cells; Clinical Immunology (2006) vol. 120, No. 3 pp. 247-259.

Witvrouw, Myriam., et al; Potent Anti-HIV (Type 1 and Type 2) Activity of Polyoxometalates: Structure—Activity Relationship and Mechanism of Action; Journal of Medicinal Chemistry (2000) vol. 43, No. 5 pp. 778-783.

* cited by examiner

*Primary Examiner* — Jeffrey S. Parkin
(74) *Attorney, Agent, or Firm* — McHale & Slavin, P.A.

(57) ABSTRACT

The present invention relates specific activation of a regulatory T cell via a specific CD4 epitope and uses thereof, e.g. for the treatment of an autoimmune disease or an allergy or asthma or graft rejection or tolerance induction.

35 Claims, 3 Drawing Sheets

SEQUENCE LISTING

```
<160> NUMBER OF SEQ ID NOS: 10

<210> SEQ ID NO 1
<211> LENGTH: 31
<212> TYPE: PRT
<213> ORGANISM: human

<400> SEQUENCE: 1

Lys Asn Ser Asn Gln Ile Lys Ile Leu Gly Asn Gln Gly Ser Phe Leu
1               5                   10                  15

Thr Lys Gly Pro Ser Lys Leu Asn Asp Arg Ala Asp Ser Arg Arg
            20                  25                  30


<210> SEQ ID NO 2
<211> LENGTH: 458
<212> TYPE: PRT
<213> ORGANISM: human

<400> SEQUENCE: 2

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270
```

```
Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
        435                 440                 445

His Arg Phe Gln Lys Thr Cys Ser Pro Ile
    450                 455


<210> SEQ ID NO 3
<211> LENGTH: 31
<212> TYPE: PRT
<213> ORGANISM: HIV-1
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 3
```

```
Trp Gln Xaa Xaa Gly Xaa Ala Xaa Tyr Ala Xaa Pro Ile Xaa Gly Xaa
1               5                   10                  15

Xaa Xaa Cys Xaa Ser Asn Ile Thr Gly Xaa Xaa Leu Thr Xaa Asp
            20                  25                  30


<210> SEQ ID NO 4
<211> LENGTH: 31
<212> TYPE: PRT
<213> ORGANISM: HIV-1

<400> SEQUENCE: 4

Trp Gln Gly Ala Gly Gln Ala Met Tyr Ala Pro Pro Ile Ser Gly Lys
1               5                   10                  15

Ile Asn Cys Val Ser Asn Ile Thr Gly Ile Leu Leu Thr Arg Asp
            20                  25                  30


<210> SEQ ID NO 5
<211> LENGTH: 31
<212> TYPE: PRT
<213> ORGANISM: HIV-1

<400> SEQUENCE: 5

Trp Gln Glu Val Gly Lys Ala Met Tyr Ala Pro Pro Ile Ser Gly Gln
1               5                   10                  15

Ile Arg Cys Ser Ser Asn Ile Thr Gly Leu Leu Leu Thr Arg Asp
            20                  25                  30


<210> SEQ ID NO 6
<211> LENGTH: 31
<212> TYPE: PRT
<213> ORGANISM: HIV-1

<400> SEQUENCE: 6

Trp Gln Lys Val Gly Lys Ala Met Tyr Ala Pro Pro Ile Glu Gly Gln
1               5                   10                  15

Ile Arg Cys Ser Ser Asn Ile Thr Gly Leu Leu Leu Thr Arg Asp
            20                  25                  30


<210> SEQ ID NO 7
<211> LENGTH: 31
<212> TYPE: PRT
<213> ORGANISM: HIV-1
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: misc_feature
<222> LOCATION: (20)..(20)
```

```
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 7

Trp Gln Xaa Xaa Gly Xaa Ala Xaa Tyr Ala Xaa Pro Ile Xaa Gly Xaa
1               5                   10                  15

Xaa Xaa Cys Xaa Ser Lys Ile Thr Gly Xaa Xaa Leu Thr Xaa Asp
            20                  25                  30


<210> SEQ ID NO 8
<211> LENGTH: 31
<212> TYPE: PRT
<213> ORGANISM: HIV-1
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 8

Trp Gln Xaa Xaa Gly Xaa Ala Xaa Tyr Ala Xaa Pro Thr Xaa Gly Xaa
1               5                   10                  15

Xaa Xaa Cys Xaa Ser Asn Ile Thr Gly Xaa Xaa Leu Thr Xaa Asp
            20                  25                  30


<210> SEQ ID NO 9
<211> LENGTH: 31
<212> TYPE: PRT
<213> ORGANISM: HIV-1
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
```

<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 9

```
Trp Gln Xaa Xaa Gly Xaa Ala Xaa Tyr Thr Xaa Pro Ile Xaa Gly Xaa
1               5                   10                  15

Xaa Xaa Cys Xaa Ser Asn Ile Thr Gly Xaa Xaa Leu Thr Xaa Asp
            20                  25                  30
```

<210> SEQ ID NO 10
<211> LENGTH: 31
<212> TYPE: PRT
<213> ORGANISM: HIV-1
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid -continued

```
<400> SEQUENCE: 10

Val Ala Xaa Xaa Arg Xaa Ala Xaa Tyr Ala Xaa Pro Ile Xaa Arg Xaa
1               5                   10                  15

Xaa Xaa Cys Xaa Ser Asn Ile Thr Gly Xaa Xaa Leu Thr Xaa Asp
            20                  25                  30
```

SCREENING METHOD FOR THE IDENTIFICATION OF AGENTS CAPABLE OF ACTIVATING CD4+CD25+ REGULATORY T-CELLS THROUGH INTERACTIONS WITH THE HIV-1 GP120 BINDING SITE ON CD4

This application is the national phase entry under 35 U.S.C. §371 of International Application No. PCT/EP2008/051144, filed Jan. 30, 2008, which claims priority to European Patent Applications No. 07101604.2, filed Feb. 1, 2007 and 07122424.0, filed Dec. 5, 2007, which are hereby incorporated by reference in their entireties.

INTRODUCTION

Asthma, an allergic disease, transplant rejection and an autoimmune disease have one fundamental principle in common, they all are triggered by an imbalanced immune system which reacts hyperactive against a specific exogenic and/or endogenic challenge and therewith contributes significantly to the disease status.

It is generally accepted that such aberrations of the immune system have a common pathophysiological mechanism triggered by hyper-responsive effector T cells playing a central role in immune reactivity. Effector T cell-directed immunomodulation therefore is the key to successful treatment of asthma, an autoimmune condition, prevention of graft vs. host disease (GVHD) and prevention of graft rejection.

T lymphocytes, designated as regulatory T cells ("Treg cells") control immune responses by suppressing the effector function of $CD4^+$ T cells and $CD8^+$ T cells (Shevach 2002). Different subsets of Treg cells have been described. These include but are not limited to (i) $CD4^+CD25^+$ Treg cells—also designated as "naturally occurring Treg cells" (Sakaguchi 2005), (ii) Tr1 (Roncarolo et al. 2001) and (iii) Th3 (Weiner 2001). Tr1 and Th3 are induced in the periphery, whereas $CD4^+CD25^+$ Treg cells develop in the thymus and constitute 5-10% of peripheral $CD4^+$ T cells in healthy man. At least in vitro these cells are anergic, produce minimal amounts of cytokines and exert their suppressive effects only upon stimulation and in a strictly cell-contact dependent manner. Tr1 and Th3 exert their suppressive activity by production of IL-10 and TGF-beta, respectively (Shevach 2002).

Genetic defects that primarily affect Treg cell development or function should cause autoimmune and inflammatory aberrations. IPEX syndrome (immunodysregulation, polyendocrinopathy and enteropathy, X-linked), a rare recessive disorder in humans is caused by a mutation in the gene of the transcription factor FOXP3 and subsequent absence of Treg cells. IPEX shows aggressive autoimmunity, severe eczema, elevated IgE levels, eosinophilia and food allergies and early death (Fontenot and Rudensky 2005).

Data from the literature show that Treg cells play an important role in asthma and autoimmune diseases and have a potential for treatment of GVHD and therewith transplantation tolerance (Robinson 2004, Sakaguchi 2005).

Therefore, attempts have been started to use Treg cells as a therapeutic agent for patients with established autoimmune disease (Horwitz et al. 2003). It is believed that said patients lack sufficient Treg cells or do have impaired Treg cell function resulting in misdirected and uncontrolled effector T cell activity. The previous thinking for solving this problem is administering Treg cells to a said patient. Since Treg cells are rare in peripheral blood clinical application of human Treg cells depends on highly expensive ex vivo expansion of Treg cells (Hoffmann et al. 2004, Horwitz et al. 2003, Tang et al. 2003, Zheng et al. 2004). Bluestone and Tang went one step further: They are trying to solve the problem by not only increasing the amount of Treg cells for therapy but enhancing suppressive activity of Treg cells by activating Treg cells via triggering of the T cell receptor (TCR) by an anti-CD3 antibody (Bluestone and Tang 2004). This approach resembles by far no Treg cell specific activation as anti-CD3 activates all T cell receptor-expressing cells which bears the obstacle that anti-CD3 treatment induces effector T cell function probably leading to uncontrolled proliferation and non-specific pro-inflammatory cytokine production and exaggeration of pathology. To circumvent this unwanted triggering of effector T cells Treg cells have to be highly purified and activated ex vivo with anti-CD3 which again is a highly expensive and laborious procedure. In addition, the absence of a Treg cell specific marker makes it difficult to achieve high purity of Treg cells.

Therefore, it is a primary goal to identify a substance which can activate Treg cells specifically without stimulating the immune system any further and therefore would provide a basis for a direct in vivo application without money consuming ex vivo treatments.

There is some information in the prior art how Treg cells possibly can be activated, e.g. nonspecifically via CD3 (Thornton and Shevach 1998), or via CD28/B7 pathway (Shevach 2002, Bluestone and Tang 2004, Hunig and Dennehy 2005), or via CD4 (WO04083247). So far all this solutions do not result in a specific Treg cell activation.

DESCRIPTION OF THE INVENTION

The present invention bases on the new finding that a specific epitope of CD4 triggers activation of Treg cells. Said epitope overlaps with the known HIV-1 gp120-binding site but surprisingly binding to this site causes Treg cell activation. This finding was totally unexpected for the following reasons: Until now Treg cell activation via CD4 was attributed to a different epitope to which the monoclonal antibody BF5 (WO04083247) binds. —Carriere et al., 1995 have investigated that the binding site of BF5 on CD4 is completely independent of the HIV-1 gp120-binding site. —Unexpectedly, despite reports in the literature on direct anergizing and blocking of CD4 on T cell function by HIV-1 gp120 (Diamond et al. 1988), we found an activating property of HIV-1 gp120 on CD4 of Treg cells.

The present invention discloses a physiologically active CD4 epitope on a Treg cell which triggers suppressive activity of a Treg cell. The epitope of the present invention has been identified as a region on the human CD4 protein (SEQ ID NO.: 2) spanning amino acid position No. 54 to 84 of SEQ ID NO.:2. Those 31 amino acids are explicitly given in SEQ ID NO.:1.

A preferred peptide which is a CD4 fragment according to the present invention is selected from a group consisting of an isolated peptide spanning amino acid No. 1-31 of SEQ ID NO 1, No. 26 to 458 of SEQ ID NO.: 2, No. 26 to 419 of SEQ ID NO.:2, No. 26 to 207 of SEQ ID NO.: 2, No. 26 to 131 of SEQ ID NO.: 2 and No. 46 to 89 of SEQ ID NO.: 2. All said peptides are additionally characterized in that they all do harbor the critical amino acid Phenylalanine at residue 68 of SEQ ID NO.: 2.

The finding that the epitope given in SEQ ID NO.:1 is a key to activate a Treg cell provides a basis for several uses, e.g.:

Methods for identification of a substance which can activate a regulatory T cell (Treg cell). Such a substance is designated "Treg cell activator" of the present invention which is useful for the treatment of a disease of the invention which is a disease in which increase of activated regulatory T cells (Treg cells) can improve clinical picture wherein such a disease is (i) a non-autoimmune inflammatory disease: asthma, allergic asthma, respiratory allergy, allergic rhinoconjunctivitis, allergic alveolitis, contact allergy, atopic dermatitis, neurodermatitis, food allergy, graft-versus-host disease, non-autoimmune inflammatory bowel disease, acute respiratory distress syndrome, acute inflammatory pancreatitis, burns, wound healing, skin scarring disorders, sarcoidosis, Behcet's disease or Sweet's syndrome; (ii) an autoimmune inflammatory disease: rheumatoid arthritis, rheumatic fever, systemic lupus erythematosus, ulcerative colitis, Crohn's disease, autoimmune inflammatory bowel disease, diabetes type I, gastritis, autoimmune atrophic gastritis, autoimmune hepatitis, Hashimoto's thyroiditis, thyreoiditis, multiple sclerosis, myasthenia gravis, autoimmune haemolytic anemia, Addison's disease, scleroderma, Goodpasture's syndrome, Guillain-Barre syndrome, Graves' disease, glomerulonephritis, psoriasis, pemphigus vulgaris, pemphigoid, vitiligo, idiopathic leukopenia, Sjogren's syndrome or Wegener's granulomatosis; (iii) an inflammatory disease due to organ transplantation; (iv) a bone marrow transplantation; or (v) a disease due to exogenously administered self or exogenously administered non-autologous recombinant polypeptide.

A "substance" of the present invention can be used in a method according to the present invention. The meaning of the term substance according to the present invention includes but is not limited to a peptide, a scaffolded peptide, an antibody, a fragment of an antibody, a nucleic acid molecule, a ribozyme, an organic compound or an inorganic compound.

In a second aspect, the new epitope serves as the basis for the synthesis of a new tool which can be used e.g. in a competition assay or screening assay according to the present invention for determining whether a substance can activate a regulatory T cell (Treg cell) via interaction with the epitope as set forth in SEQ ID No.:1. Such a tool is a peptide of the present invention which is an isolated peptide spanning amino acid No. 1-31 of SEQ ID NO 1, or No. 26 to 458 of SEQ ID NO.: 2, or No. 26 to 419 of SEQ ID NO.:2, or No. 26 to 207 of SEQ ID NO.: 2, or No. 26 to 131 of SEQ ID NO.: 2 or No. 46 to 89 of SEQ ID NO.: 2, or is an isolated peptide spanning amino acid No. 1 to 31 of SEQ ID NO.: 1 and having additional up-stream and/or downstream amino acids with the prerequisite that the additional amino acids do not hinder binding of a substance to the amino acid stretch as set forth in SEQ ID No.:1. A preferred peptide according to the present invention consist of the peptide as set forth in SEQ ID NO.:1 and additionally consist of an additional up-stream amino acid or amino acid stretch which is selected from a group consisting of the amino acid or amino acid stretch as set forth in SEQ ID NO.: 2 at position 53, at position 52-53, at position 51-53, at position 50-53, at position 49-53, at position 48-53, at position 47-53, at position 46-53, at position 45-53, at position 44-53, at position 43-53, at position 42-53, at position 41-53, at position 40-53, at position 39-53, at position 38-53, at position 37-53, at position 36-53, at position 35-53, at position 34-53, at position 33-53, at position 32-53, at position 31-53, at position 30-53, at position 29-53, at position 28-53, at position 27-53, at position 26-53, at position 25-53, at position 24-53, at position 23-53, at position 22-53, at position 21-53, at position 20-53, at position 19-53, at position 18-53, at position 17-53, at position 16-53, at position 15-53, at position 14-53, at position 13-53, at position 12-53, at position 11-53, at position 10-53, at position 9-53, at position 8-53, at position 7-53, at position 6-53, at position 5-53, at position 4-53, at position 3-53, at position 2-53, and at position 1-53.

A further preferred peptide according to the present invention consists of the peptide which is mentioned as "preferred peptide" in the paragraph above and additionally consists of at least one additional downstream amino acid as given in SEQ ID NO.: 2 at position 85, or additionally consists of amino acids as given in SEQ ID NO.:2 at position 85 to n, wherein n is an integer between 86-458, i.e. position 85 to 86, 85 to 87, 85 to 88, 85 to 89, 85 to 90, 85 to 91, 85 to 92, 85 to 93, 85 to 94, 85 to 95, 85 to 96, 85 to 97, 85 to 98, 85 to 99, 85 to 100, 85 to 101, 85 to 102, 85 to 103, 85 to 104, 85 to 105, 85 to 106, 85 to 107, 85 to 108, 85 to 109, 85 to 110, 85 to 111, 85 to 112, 85 to 113, 85 to 114, 85 to 115, 85 to 116, 85 to 117, 85 to 118, 85 to 119, 85 to 120, 85 to 121, 85 to 122, 85 to 123, 85 to 124, 85 to 125, 85 to 126, 85 to 127, 85 to 128, 85 to 129, 85 to 130, 85 to 131, 85 to 132, 85 to 133, 85 to 134, 85 to 135, 85 to 136, 85 to 137, 85 to 138, 85 to 139, 85 to 140, 85 to 141, 85 to 142, 85 to 143, 85 to 144, 85 to 145, 85 to 146, 85 to 147, 85 to 148, 85 to 149, 85 to 150, 85 to 151, 85 to 152, 85 to 153, 85 to 154, 85 to 155, 85 to 156, 85 to 157, 85 to 158, 85 to 159, 85 to 160, 85 to 161, 85 to 162, 85 to 163, 85 to 164, 85 to 165, 85 to 166, 85 to 167, 85 to 168, 85 to 169, 85 to 170, 85 to 171, 85 to 172, 85 to 173, 85 to 174, 85 to 175, 85 to 176, 85 to 177, 85 to 178, 85 to 179, 85 to 180, 85 to 181, 85 to 182, 85 to 183, 85 to 184, 85 to 185, 85 to 186, 85 to 187, 85 to 188, 85 to 189, 85 to 190, 85 to 191, 85 to 192, 85 to 193, 85 to 194, 85 to 195, 85 to 196, 85 to 197, 85 to 198, 85 to 199, 85 to 200, 85 to 201, 85 to 202, 85 to 203, 85 to 204, 85 to 205, 85 to 206, 85 to 207, 85 to 208, 85 to 209, 85 to 210, 85 to 211, 85 to 212, 85 to 213, 85 to 214, 85 to 215, 85 to 216, 85 to 217, 85 to 218, 85 to 219, 85 to 220, 85 to 221, 85 to 222, 85 to 223, 85 to 224, 85 to 225, 85 to 226, 85 to 227, 85 to 228, 85 to 229, 85 to 230, 85 to 231, 85 to 232, 85 to 233, 85 to 234, 85 to 235, 85 to 236, 85 to 237, 85 to 238, 85 to 239, 85 to 240, 85 to 241, 85 to 242, 85 to 243, 85 to 244, 85 to 245, 85 to 246, 85 to 247, 85 to 248, 85 to 249, 85 to 250, 85 to 251, 85 to 252, 85 to 253, 85 to 254, 85 to 255, 85 to 256, 85 to 257, 85 to 258, 85 to 259, 85 to 260, 85 to 261, 85 to 262, 85 to 263, 85 to 264, 85 to 265, 85 to 266, 85 to 267, 85 to 268, 85 to 269, 85 to 270, 85 to 271, 85 to 272, 85 to 273, 85 to 274, 85 to 275, 85 to 276, 85 to 277, 85 to 278, 85 to 279, 85 to 280, 85 to 281, 85 to 282, 85 to 283, 85 to 284, 85 to 285, 85 to 286, 85 to 287, 85 to 288, 85 to 289, 85 to 290, 85 to 291, 85 to 292, 85 to 293, 85 to 294, 85 to 295, 85 to 296, 85 to 297, 85 to 298, 85 to 299, 85 to 300, 85 to 301, 85 to 302, 85 to 303, 85 to 304, 85 to 305, 85 to 306, 85 to 307, 85 to 308, 85 to 309, 85 to 310, 85 to 311, 85 to 312, 85 to 313, 85 to 314, 85 to 315, 85 to 316, 85 to 317, 85 to 318, 85 to 319, 85 to 320, 85 to 321, 85 to 322, 85 to 323, 85 to 324, 85 to 325, 85 to 326, 85 to 327, 85 to 328, 85 to 329, 85 to 330, 85 to 331, 85 to 332, 85 to 333, 85 to 334, 85 to 335, 85 to 336, 85 to 337, 85 to 338, 85 to 339, 85 to 340, 85 to 341, 85 to 342, 85 to 343, 85 to 344, 85 to 345, 85 to 346, 85 to 347, 85 to 348, 85 to 349, 85 to 350, 85 to 351, 85 to 352, 85 to 353, 85 to 354, 85 to 355, 85 to 356, 85 to 357, 85 to 358, 85 to 359, 85 to 360, 85 to 361, 85 to 362, 85 to 363, 85 to 364, 85 to 365, 85 to 366, 85 to 367, 85 to 368, 85 to 369, 85 to 370, 85 to 371, 85 to 372, 85 to 373, 85 to 374, 85 to 375, 85 to 376, 85 to 377, 85 to 378, 85 to 379, 85 to 380, 85 to 381, 85 to 382, 85 to 383, 85 to 384, 85 to 385, 85 to 386, 85 to 387, 85 to 388, 85 to 389, 85 to 390, 85 to 391, 85 to 392, 85 to 393, 85 to 394, 85 to 395, 85 to 396, 85 to 397, 85 to 398, 85 to 399, 85 to 400, 85 to 401, 85 to 402, 85 to 403, 85 to 404, 85 to 405, 85 to 406, 85 to 407, 85 to 408, 85 to 409, 85 to 410, 85 to 411, 85 to 412, 85 to 413, 85 to 414, 85 to 415, 85 to 416, 85 to 417, 85 to 418, 85 to 419, 85 to 420, 85 to 421, 85 to 422, 85 to 423, 85 to 424, 85 to 425, 85 to 426, 85 to 427, 85 to 428, 85 to 429, 85 to 430, 85 to 431, 85 to 432, 85 to 433, 85 to 434, 85 to 435, 85 to 436, 85 to 437, 85 to 438, 85 to 439, 85 to 440, 85 to 441, 85 to 442, 85 to 443, 85 to 444, 85 to 445, 85 to 446, 85 to 447, 85 to 448, 85 to 449, 85 to 450, 85 to 451, 85 to 452, 85 to 453, 85 to 454, 85 to 455, 85 to 456, 85 to 457, or 85 to 458.

Additionally, the finding that the epitope given in SEQ ID NO.:1 is a key to activate a Treg cell is a link between two different up to now unrelated technical fields, namely that of (a) HIV-1 related diseases with (b) diseases according to the present invention e.g autoimmune disease, allergy, asthma, graft rejection and a diseases due to lacking immunotolerance caused by organ transplantation or by therapeutical administration of a non-self or self biological entity to a human in need thereof and therewith allows a bundle of new uses as explained in the following:

The epitope given in SEQ ID NO.:1 is not only a further epitope which can be used to activate Treg cells. HIV-1 gp120 interacts with CD4 of T cells and therewith enables virus entry into a $CD4^+$ cell (Klatzmann et al. 1984). The finding that epitope given in SEQ ID NO.:1 harbors the high affinity binding site on CD4 to which human immune deficiency virus 1 (HIV-1) glycoprotein gp120 binds (Jameson et al. 1988, Arthos et al. 1989) offers a further advantage. It provides the basis to bring together the findings of two different unrelated technical fields that of i.e. HIV-1 related diseases with diseases according to the present invention.

To alleviate the worldwide HIV-1 problem many efforts have been made to identify a substance which is able to inhibit HIV-1 entry into a $CD4^+$ cell. As a result thereof, so called HIV-1 attachment or entry inhibitors are known in the art.

The keyhole which allows HIV-1 to enter the cell can be used as the keyhole to activate Treg cells. Therefore, substances known in the art to interfere with HIV-1 attachment and cell entry (Markovic and Clouse 2004, Castagna et al. 2005), like e.g. HIV-1 gp120 itself, derivatives thereof, peptidomimetics, antibodies, aptamers or any low molecular weight (LMW) compound directed against the binding site of HIV-1 gp120 on CD4 could possibly be useful to activate a Treg cell and therewith can be useful for the treatment of a disease according to the present invention (HIV-1 gp120 is well-known in the art and its amino acid sequence as well as the respective gene has been published since years (Muesing et al. 1985, Starcich et al. 1986, Jeffs et al. 1996). Additionally, methods for producing HIV-1 gp120 are known (Lasky et al. 1986, Leonard et al. 1990, Culp et al. 1991, Jeffs et al. 1996).

A substance which can interfere with HIV-1 attachment and/or cell entry is commonly named HIV-1 attachment inhibitor or entry inhibitor. Such a substance, do either bind to (i) HIV-1, or (ii) to CD4, or (iii) HIV-1 and CD4 or (iv) co-receptor e.g. CCR5 or CXCR4. Such an inhibitor can be according to the present invention useful for the treatment of diseases according to the present invention like e.g. an autoimmune disease, an allergy, asthma or GVHD if it exerts property (ii) or (iii) and activates a Treg cell. To determine whether such an inhibitor can be useful for a said disease the present invention discloses several assays which allow to determine whether a substance identified in the technical field of HIV-1 research to interfere with HIV-1 attachment and/or cell entry can be useful in the other above-mentioned technical fields like that of autoimmune diseases or allergies or asthma or organ transplantation. Therefore, the present invention teaches a short cut for identifying a substance which can be useful for the treatment of a disease according to the present invention.

Identification of a substance which can be used as a medicament in a specific disease usually depends on resource consuming high through put screenings (HTS). Determination whether a substance can activate a Treg cell currently depends on a cellular assay comprising a Treg cell. Since Treg cells can only be provided in small amounts large screening campaigns or even an HTS therewith are not feasible today. The teaching of the present invention allows to circumvent this obstacles since the present invention allows to pre-select substances which possible can activate a Treg cell. According to the present invention an appropriate pre-selected substance is (i) proven to interact at least with epitope (SEQ ID NO.:1), and/or is (ii) known from HIV-1 research as HIV-1 attachment inhibitor or entry inhibitor or synthetic mimetics of the CD4 binding site of HIV-1 gp120.

It is state of the art to determine whether a substance can interact with a given peptide and therewith a given epitope even in an HTS format. Concerning the present invention this can be performed for example in an in vitro competition type assay comprising a peptide spanning at least amino acids as set forth in SEQ ID NO.: 1 mixed with an unlabeled substance to be tested and subsequently with a labeled substance which is known to bind the peptide (e.g. HIV-1 gp120) under conditions which allow binding of the peptide with the labeled substance. A substance which interact with the peptide will compete with the labeled substance and is identifiable by a rendered readout, which can be performed e.g. by measuring the bound or free labeled substance.

Such a type of assay for determining whether a substance can interact with a specific peptide, i.e. epitope is not restricted to in vitro assays since cellular assays for achieving such an information on a substance or other in vitro formats are well known in the art and broadly used.

In one embodiment the present invention concerns a method for determining whether a substance which can interfere with the interaction of HIV-1 gp120 with CD4 can be useful for positively influence a disease in which increase of activated regulatory T cells (Treg cells) can improve clinical picture comprising:

(a) providing a solution comprising a Treg cell, wherein a Treg cell is preferably a $CD4^+CD25^+$ Treg cell or a Tr1 cell or a Th3 cell. Said solution does more preferably comprise additionally an inactivated syngenic CD3-depleted PBMC (peripheral blood mononuclear cell which has preferably been inactivated via irradiation or via mitomycin C) or a dendritic cell (DC) and an allogeneic CD8+ T cell or an allogeneic CD4+ T cell, (b) adding a substance to be tested under conditions which allow interaction of the substance with a Treg cell, (c) measuring whether a Treg cell has been activated, wherein an activated Treg cell identifies the substance as a Treg cell activator.

Said measuring can be performed using a suitable read-out system such as:

(i) measuring whether a $CD8^+$ T cell has been suppressed—which preferably can be determined by measuring inhibited proliferation of the $CD8^+$ T cell or by measuring reduced CD25 expression of the $CD8^+$ T cell, or by measuring inhibited cytokine production of the $CD8^+$ T cell wherein a suitable cytokine is IFNγ or IL2, or TNFα—wherein a suppressed $CD8^+$ T cell identifies an activated Treg cell and therewith identifies the substance as a Treg cell activator, or by (ii) measuring whether a $CD4^+$ T cell has been suppressed—which preferably can be determined by measuring inhibited proliferation of the $CD4^+$ T cell or by measuring reduced CD25 expression of the $CD4^+$ T cell, or by measuring inhibited cytokine production of the $CD4^+$ T cell wherein a suitable cytokine is IFNγ or IL2, or TNFα—wherein a suppressed CD4$^+$ T cell identifies an activated Treg cell and therewith identifies the substance as a Treg cell activator, or by (iii) measuring the amount of intracellular cAMP (i.e. cytosolic cAMP) and wherein an increased amount of intracellular cAMP is indicative for an activated Treg cell and therewith identifies the substance as a Treg cell activator.

A disease according to the method above in which increase of activated regulatory T cells (Treg cells) can improve clinical picture is (i) a non-autoimmune inflammatory disease: asthma, allergic asthma, respiratory allergy, allergic rhinoconjunctivitis, allergic alveolitis, contact allergy, atopic dermatitis, neurodermatitis, food allergy, graft-versus-host disease, non-autoimmune inflammatory bowel disease, acute respiratory distress syndrome, acute inflammatory pancreatitis, burns, wound healing, skin scarring disorders, sarcoidosis, Behcet's disease or Sweet's syndrome; (ii) an autoimmune inflammatory disease: rheumatoid arthritis, rheumatic fever, systemic lupus erythematosus, ulcerative colitis, Crohn's disease, autoimmune inflammatory bowel disease, diabetes type I, gastritis, autoimmune atrophic gastritis, autoimmune hepatitis, Hashimoto's thyroiditis, thyreoiditis, multiple sclerosis, myasthenia gravis, autoimmune haemolytic anemia, Addison's disease, scleroderma, Goodpasture's syndrome, Guillain-Barre syndrome, Graves' disease, glomerulonephritis, psoriasis, pemphigus vulgaris, pemphigoid, vitiligo, idiopathic leukopenia, Sjogren's syndrome or Wegener's granulomatosis; (iii) an inflammatory disease due to organ transplantation; (iv) a bone marrow transplantation; or (v) a disease due to exogenously administered self or exogenously administered non-autologous recombinant polypeptide.

As the readout systems as mentioned in (i) and (ii) above are methods in which several steps have to be performed a specific new test system has been invented to determine in only one step whether a Treg cell has been activated which is mentioned in (iii) above. Basing on the surprising finding that the activation status of a Treg cell strongly correlates with the amount of intracellular cAMP the present invention provides for a specific method for determining whether a Treg cell has been activated which comprises:

(a) providing a first solution comprising a Treg cell,
(b) providing a second solution comprising a Treg cell,
(c) manipulation the first solution by adding at least a test substance,
(d) determining the amount of intracellular cAMP of the first and the second solution wherein an increased amount of intracellular cAMP of the first solution is indicative for an activated Treg cell.

In a more preferred method the solution of (a) does not only contain a Treg cell but also an inactivated syngenic CD3-depleted PBMC (peripheral blood mononuclear cell) or a dendritic cell (DC) and an allogeneic CD8$^+$ T cell or an allogeneic CD4$^+$ T cell. These cells when combined in one solution with a activated Treg cell do additionally increase intracellular cAMP amount and therewith lead to a more sensitive readout system.

In a further embodiment the present invention concerns a method for determining whether a substance can activate a Treg cell via interaction with the HIV-1 gp120-binding site of CD4, comprising:

(a) pre-selecting a substance which can interact with the HIV-1 gp120-binding site of CD4 (for a method for pre-selection please see below),
(b) providing a solution comprising a Treg cell wherein a Treg cell is preferably a CD4$^+$CD25$^+$ Treg cell or a Tr1 cell or a Th3 cell. Said solution does more preferably comprise additionally an inactivated syngenic CD3-depleted PBMC (peripheral blood mononuclear cell) which has preferably been inactivated via irradiation or via mitomycin C) or a dendritic cell (DC) and an allogeneic CD8+ T cell or an allogeneic CD4+ T cell,
(c) adding a pre-selected substance according to (a) under conditions which allow interaction of the substance with a Treg cell,
(d) measuring whether a Treg cell has been activated, wherein an activated Treg cell identifies the substance as a Treg cell activator. Said measuring can be performed using a suitable read-out system such as:

(i) measuring whether a CD8$^+$ T cell has been suppressed—which preferably can be determined by measuring inhibited proliferation of the CD8$^+$ T cell or by measuring reduced CD25 expression of the CD8$^+$ T cell, or by measuring inhibited cytokine production of the CD8$^+$ T cell wherein a suitable cytokine is IFNγ or IL2, or TNFα—wherein a suppressed CD8$^+$ T cell identifies an activated Treg cell and therewith identifies the substance as a Treg cell activator, or by (ii) measuring whether a CD4$^+$ T cell has been suppressed—which preferably can be determined by measuring inhibited proliferation of the CD4$^+$ T cell or by measuring reduced CD25 expression of the CD4$^+$ T cell, or by measuring inhibited cytokine production of the CD4$^+$ T cell wherein a suitable cytokine is IFNγ or IL2, or TNFα—wherein a suppressed CD4$^+$ T cell identifies an activated Treg cell and therewith identifies the substance as a Treg cell activator, or by (iii) measuring the amount of intracellular cAMP and wherein an increased amount of intracellular cAMP is indicative for an activated Treg cell and therewith identifies the substance as a Treg cell activator.

The present invention also provides for a method which allow to identify a substance which can interact with the HIV-1 gp120-binding site of CD4 and therewith can be used for pre-selecting a substance which can interact with the HIV-1 gp120-binding site of CD4. The method comprises:

(a) providing a first solution comprising CD4,
(b) providing a second solution comprising CD4,
(c) adding to the first solution a substance to be tested and HIV-1 gp120 under conditions which allow binding of HIV-1 gp120 with CD4,
(d) adding to the second solution HIV-1 gp120 under conditions like (c) allowing binding of HIV-1 gp120 with CD4,
(e) measuring in the first and in the second solution whether the HIV-1 gp120 has bound to the CD4 wherein a reduced amount of bound HIV-1 gp120 in the first solution indicates that the substance can interact with HIV-1 gp120-binding site of CD4.

This pre-selecting method can additionally be performed according to the present invention if instead of CD4 a peptide is used which comprises the amino acid stretch as set forth in SEQ ID NO. 1 or instead of CD4 a peptide is used as set forth in SEQ ID NO.:1. In a more preferred method according to the present invention instead of HIV-1 gp120 a peptide is used selected from a group consisting of a peptide comprising the amino acid sequence as set forth in SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, and SEQ ID NO.: 10 or a peptide is used selected from a group consisting of a peptide consisting of the amino acid sequence as set forth in SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, and SEQ ID NO.: 10.

In a further embodiment the present invention concerns a method for determining whether a substance can activate a regulatory T cell (Treg) via interaction with the epitope as set forth in SEQ ID NO: 1 comprising:

(a) providing a first solution comprising a Treg cell, wherein a Treg cell is preferably a $CD4^{+}CD25^{+}$ Treg cell or a Tr1 cell or a Th3 cell. Said solution does more preferably comprise additionally an inactivated syngenic CD3-depleted PBMC (peripheral blood mononuclear cell which has preferably been inactivated via irradiation or via mitomycin C) or a dendritic cell (DC) and an allogeneic CD8+ T cell or an allogeneic CD4+ T cell, (b) adding a substance to be tested under conditions which allow interaction of the substance with a Treg cell, (c) measuring whether a Treg cell of the first solution has been activated, (d) providing a second solution comprising a Treg cell, wherein a Treg cell is preferably a $CD4^{+}CD25^{+}$ Treg cell or a Tr1 cell or a Th3 cell. Said solution does more preferably comprise additionally an inactivated syngenic CD3-depleted PBMC (peripheral blood mononuclear cell which has preferably been inactivated via irradiation or via mitomycin C) or a dendritic cell (DC) and an allogeneic CD8+ T cell or an allogeneic CD4+ T cell, (e) adding the substance to be tested and a peptide comprising an amino acid sequence as set forth in SEQ ID NO: 1 under conditions like (b), (f) measuring whether a Treg cell of the second solution has been activated, Said measuring can be performed using a suitable readout system such as:

(i) measuring whether a $CD8^{+}$ T cell has been suppressed—which preferably can be determined by measuring inhibited proliferation of the $CD8^{+}$ T cell or by measuring reduced CD25 expression of the $CD8^{+}$ T cell, or by measuring inhibited cytokine production of the $CD8^{+}$ T cell wherein a suitable cytokine is IFNγ or IL2, or TNFα—wherein a suppressed $CD8^{+}$ T cell identifies an activated Treg cell and therewith identifies the substance as a Treg cell activator, or by (ii) measuring whether a $CD4^{+}$ T cell has been suppressed—which preferably can be determined by measuring inhibited proliferation of the $CD4^{+}$ T cell or by measuring reduced CD25 expression of the $CD4^{+}$ T cell, or by measuring inhibited cytokine production of the $CD4^{+}$ T cell wherein a suitable cytokine is IFNγ or IL2, or TNFα—wherein a suppressed $CD4^{+}$ T cell identifies an activated Treg cell and therewith identifies the substance as a Treg cell activator, or by (iii) measuring the amount of intracellular cAMP and wherein an increased amount of intracellular cAMP is indicative for an activated Treg cell and therewith identifies the substance as a Treg cell activator;

(g) comparing results obtained from (c) with those obtained from (f) wherein a reduced activation of (f) identifies the substance as a Treg cell activator which activates a Treg cell via interaction with the epitope as set forth in SEQ ID NO: 1.

In a more preferred method in step (e) of above mentioned method the peptide used is selected from a group consisting of an isolated peptide spanning amino acid No. 1-31 of SEQ ID NO 1, No. 26 to 458 of SEQ ID NO.: 2, No. 26 to 419 of SEQ ID NO.:2, No. 26 to 207 of SEQ ID NO.: 2, No. 26 to 131 of SEQ ID NO.: 2 and No. 46 to 89 of SEQ ID NO.: 2 or the peptide used is an isolated peptide spanning amino acid No. 1 to 31 of SEQ ID NO.: 1 and having additional up-stream and/or downstream amino acids with the prerequisite that the additional amino acids do not hinder binding of a substance to the amino acid stretch as set forth in SEQ ID No.:1. Said additional up-stream amino acid or amino acid stretch is preferably selected from a group consisting of the amino acid or amino acid stretch as set forth in SEQ ID NO.: 2 at position 53, at position 52-53, at position 51-53, at position 50-53, at position 49-53, at position 48-53, at position 47-53, at position 46-53, at position 45-53, at position 44-53, at position 43-53, at position 42-53, at position 41-53, at position 40-53, at position 39-53, at position 38-53, at position 37-53, at position 36-53, at position 35-53, at position 34-53, at position 33-53, at position 32-53, at position 31-53, at position 30-53, at position 29-53, at position 28-53, at position 27-53, at position 26-53, at position 25-53, at position 24-53, at position 23-53, at position 22-53, at position 21-53, at position 20-53, at position 19-53, at position 18-53, at position 17-53, at position 16-53, at position 15-53, at position 14-53, at position 13-53, at position 12-53, at position 11-53, at position 10-53, at position 9-53, at position 8-53, at position 7-53, at position 6-53, at position 5-53, at position 4-53, at position 3-53, at position 2-53, and at position 1-53. A more preferred peptide does additionally comprise downstream one or more amino acids as set forth in SEQ ID NO.: 2 at position 85, or at position 85 to n, wherein n is an integer between 86-458, i.e. position 85 to 86, 85 to 87, 85 to 88, 85 to 89, 85 to 90, 85 to 91, 85 to 92, 85 to 93, 85 to 94, 85 to 95, 85 to 96, 85 to 97, 85 to 98, 85 to 99, 85 to 100, 85 to 101, 85 to 102, 85 to 103, 85 to 104, 85 to 105, 85 to 106, 85 to 107, 85 to 108, 85 to 109, 85 to 110, 85 to 111, 85 to 112, 85 to 113, 85 to 114, 85 to 115, 85 to 116, 85 to 117, 85 to 118, 85 to 119, 85 to 120, 85 to 121, 85 to 122, 85 to 123, 85 to 124, 85 to 125, 85 to 126, 85 to 127, 85 to 128, 85 to 129, 85 to 130, 85 to 131, 85 to 132, 85 to 133, 85 to 134, 85 to 135, 85 to 136, 85 to 137, 85 to 138, 85 to 139, 85 to 140, 85 to 141, 85 to 142, 85 to 143, 85 to 144, 85 to 145, 85 to 146, 85 to 147, 85 to 148, 85 to 149, 85 to 150, 85 to 151, 85 to 152, 85 to 153, 85 to 154, 85 to 155, 85 to 156, 85 to 157, 85 to 158, 85 to 159, 85 to 160, 85 to 161, 85 to 162, 85 to 163, 85 to 164, 85 to 165, 85 to 166, 85 to 167, 85 to 168, 85 to 169, 85 to 170, 85 to 171, 85 to 172, 85 to 173, 85 to 174, 85 to 175, 85 to 176, 85 to 177, 85 to 178, 85 to 179, 85 to 180, 85 to 181, 85 to 182, 85 to 183, 85 to 184, 85 to 185, 85 to 186, 85 to 187, 85 to 188, 85 to 189, 85 to 190, 85 to 191, 85 to 192, 85 to 193, 85 to 194, 85 to 195, 85 to 196, 85 to 197, 85 to 198, 85 to 199, 85 to 200, 85 to 201, 85 to 202, 85 to 203, 85 to 204, 85 to 205, 85 to 206, 85 to 207, 85 to 208, 85 to 209, 85 to 210, 85 to 211, 85 to 212, 85 to 213, 85 to 214, 85 to 215, 85 to 216, 85 to 217, 85 to 218, 85 to 219, 85 to 220, 85 to 221, 85 to 222, 85 to 223, 85 to 224, 85 to 225, 85 to 226, 85 to 227, 85 to 228, 85 to 229, 85 to 230, 85 to 231, 85 to 232, 85 to 233, 85 to 234, 85 to 235, 85 to 236, 85 to 237, 85 to 238, 85 to 239, 85 to 240, 85 to 241, 85 to 242, 85 to 243, 85 to 244, 85 to 245, 85 to 246, 85 to 247, 85 to 248, 85 to 249, 85 to 250, 85 to 251, 85 to 252, 85 to 253, 85 to 254, 85 to 255, 85 to 256, 85 to 257, 85 to 258, 85 to 259, 85 to 260, 85 to 261, 85 to 262, 85 to 263, 85 to 264, 85 to 265, 85 to 266, 85 to 267, 85 to 268, 85 to 269, 85 to 270, 85 to 271, 85 to 272, 85 to 273, 85 to 274, 85 to 275, 85 to 276, 85 to 277, 85 to 278, 85 to 279, 85 to 280, 85 to 281, 85 to 282, 85 to 283, 85 to 284, 85 to 285, 85 to 286, 85 to 287, 85 to 288, 85 to 289, 85 to 290, 85 to 291, 85 to 292, 85 to 293, 85 to 294, 85 to 295, 85 to 296, 85 to 297, 85 to 298, 85 to 299, 85 to 300, 85 to 301, 85 to 302, 85 to 303, 85 to 304, 85 to 305, 85 to 306, 85 to 307, 85 to 308, 85 to 309, 85 to 310, 85 to 311, 85 to 312, 85 to 313, 85 to 314, 85 to 315, 85 to 316, 85 to 317, 85 to 318, 85 to 319, 85 to 320, 85 to 321, 85 to 322, 85 to 323, 85 to 324, 85 to 325, 85 to 326, 85 to 327, 85 to 328, 85 to 329, 85 to 330, 85 to 331, 85 to 332, 85 to 333, 85 to 334, 85 to 335, 85 to 336, 85 to 337, 85 to 338, 85 to 339, 85 to 340, 85 to 341, 85 to 342, 85 to 343, 85 to 344, 85 to 345, 85 to 346, 85 to 347, 85 to 348, 85 to 349, 85 to 350, 85 to 351, 85 to 352, 85 to 353, 85 to 354, 85 to 355, 85 to 356, 85 to 357, 85 to 358, 85 to 359, 85 to 360, 85 to 361, 85 to 362, 85 to 363, 85 to 364, 85 to 365, 85 to 366, 85 to 367, 85 to 368, 85 to 369, 85 to 370, 85 to 371, 85 to 372, 85 to 373, 85 to 374, 85 to 375, 85 to 376, 85 to 377, 85 to 378, 85 to 379, 85 to 380, 85 to 381, 85 to 382, 85 to 383, 85 to 384, 85 to 385, 85 to 386, 85 to 387, 85 to 388, 85 to 389, 85 to 390, 85 to 391, 85 to 392, 85 to 393, 85 to 394, 85 to 395, 85 to 396, 85 to 397, 85 to 398, 85 to 399, 85 to 400, 85 to 401, 85 to 402, 85 to 403, 85 to 404, 85 to 405, 85 to 406, 85 to 407, 85 to 408, 85 to 409, 85 to 410, 85 to 411, 85 to 412, 85 to 413, 85 to 414, 85 to 415, 85 to 416, 85 to 417, 85 to 418, 85 to 419, 85 to 420, 85 to 421, 85 to 422, 85 to 423, 85 to 424, 85 to 425, 85 to 426, 85 to 427, 85 to 428, 85 to 429, 85 to 430, 85 to 431, 85 to 432, 85 to 433, 85 to 434, 85 to 435, 85 to 436, 85 to 437, 85 to 438, 85 to 439, 85 to 440, 85 to 441, 85 to 442, 85 to 443, 85 to 444, 85 to 445, 85 to 446, 85 to 447, 85 to 448, 85 to 449, 85 to 450, 85 to 451, 85 to 452, 85 to 453, 85 to 454, 85 to 455, 85 to 456, 85 to 457, or 85 to 458.

In the context of the present invention new and known substances have been examined in the assays according to the present invention. As a result thereof substances could be identified which can act as a Treg cell activator of the present invention, i.e. such a substance is able to activate a Treg cell via interaction with the Treg cell epitope as set forth in SEQ ID NO:1 which could be proven in vivo.

The Present Invention Therefore Provides for Treg Cell Activators.

Disclosed are Treg cell activators according to the invention which are structurally a peptide or a polypeptide, preferably an antibody of a binding fragment thereof or a scaffolded peptide.

The present invention further concerns a new antibody or a binding fragment thereof capable of binding to the peptide as set forth in SEQ ID NO.:1 with the proviso that the antibody or the antibody fragment is not OKT4A, OKT4D4, OKTcdr4a and not Leu3. Said disclaimed antibodies all relate to a totally different technical filed, namely HIV-1 research which is not related to the activation of Treg cells and disease according to the present invention. Even the present invention combines for the first time the technical field of (a) HIV-1 related diseases with (b) diseases according to the present invention e.g autoimmune disease, allergy, asthma, graft rejection and a diseases due to lacking immunotolerance caused by organ transplantation or by therapeutical administration of a non-self or self biological entity to a human in need thereof.

A further preferred Treg cell activator peptide is a peptide selected from a group consisting of a peptide comprising the amino acid sequence as set forth in SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, and SEQ ID NO.: 10, or is a peptide selected from a group consisting of a peptide consisting of the amino acid sequence as set forth in SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, and SEQ ID NO.: 10.

A more preferred Treg cell activator polypeptide is selected from a group consisting of: HIV-1 gp120, NSC 13778 which chemical structure is disclosed in Yang et al. 2005 on page 6124 in FIG. 1, peptide2 which presents three HIV-1 gp120 fragments bound together through conformationally flexible scaffolds which chemical structure is disclosed in Franke et al. 2007 on page 4 at the bottom of the right column, monoclonal antibody OKT4A which binds to the HIV-1 gp120-binding region of CD4 as disclosed in Mizukami et al. 1988 on page 9273 right column line 19, monoclonal antibody OKT4D which binds to the HIV-1 gp120-binding region of CD4 as disclosed in Mizukami et al. 1988 on page 9273 right column line 19, monoclonal antibody OKTcdr4a which derives from the murine OKT4a as disclosed in Moreland et al. 1998 on page 222 right column line 1, monoclonal antibody Leu3 which binds to epitope overlapping the HIV-1 gp120-binding site of CD4 as disclosed in Lohmann et al. 1992 on page 3248 left column line 7, and monoclonal antibody MAX.12H5 which binds to the CDR2-like region of CD4 as disclosed in Repke et al. 1992 on page 1809 abstract line 11 and on page 1812 left column line 37.

Each of the above mentioned Treg cell activators according to the present invention can be used as a medicament and for the preparation of a medicament for the treatment of a disease selected from a group consisting of (i) a non-autoimmune inflammatory disease: asthma, allergic asthma, respiratory allergy, allergic rhinoconjunctivitis, allergic alveolitis, contact allergy, atopic dermatitis, neurodermatitis, food allergy, graft-versus-host disease, non-autoimmune inflammatory bowel disease, acute respiratory distress syndrome, acute inflammatory pancreatitis, burns, wound healing, skin scarring disorders, sarcoidosis, Behcet's disease, Sweet's syndrome; (ii) an autoimmune inflammatory disease: rheumatoid arthritis, rheumatic fever, systemic lupus erythematosus, ulcerative colitis, Crohn's disease, autoimmune inflammatory bowel disease, diabetes type I, gastritis, autoimmune atrophic gastritis, autoimmune hepatitis, Hashimoto's thyroiditis, thyreoiditis, multiple sclerosis, myasthenia gravis, autoimmune haemolytic anemia, Addison's disease, scleroderma, Goodpasture's syndrome, Guillain-Barre syndrome, Graves' disease, glomerulonephritis, psoriasis, pemphigus vulgaris, pemphigoid, vitiligo, idiopathic leukopenia, Sjogren's syndrome, Wegener's granulomatosis; (iii) an inflammatory disease due to organ transplantation; (iv) a bone marrow transplantation; and (v) a disease due to exogenously administered self or exogenously administered non-autologous recombinant polypeptide.

An other embodiment of the present invention relates to a pharmaceutical composition comprising at least one Treg cell activator according to the present invention—preferably HIV-1 gp120—as an active ingredient and can be formulated in conventional manner. Methods for making such formulations can be found in manuals, e.g. "Remington Pharmaceutical Science". Examples for ingredients that are useful for formulating at least one substance according to the present invention are also found in WO99/18193, which is hereby incorporated by reference. The composition may be manufactured in a manner that is itself known, e.g. by mean of conventional mixing, dissolving, granulating, dragee-making, levitating, powdering, emulsifying, encapsulating, entrapping of lyophilizing processes.

In a further aspect the invention teaches a method for treating a disease which is characterized in that its clinical picture can be influenced positively by an increase of activated Treg cells which method comprises administering to a being preferably a human being in need of such a treatment a suitable amount of a pharmaceutical composition comprising at least one Treg cell activator according to the present invention, preferably HIV-1 gp120 or HIV-1 gp120 derived fragments and peptides thereof. The present invention provides therefore for a method for treating (i) a non-autoimmune inflammatory disease: asthma, allergic asthma, respiratory allergy, allergic rhinoconjunctivitis, allergic alveolitis, contact allergy, atopic dermatitis, neurodermatitis, food allergy, graft-versus-host disease, non-autoimmune inflammatory bowel disease, acute respiratory distress syndrome, acute inflammatory pancreatitis, burns, wound healing, skin scarring disorders, sarcoidosis, Behcet's disease or Sweet's syndrome; (ii) an autoimmune inflammatory disease: rheumatoid arthritis, rheumatic fever, systemic lupus erythematosus, ulcerative colitis, Crohn's disease, autoimmune inflammatory bowel disease, diabetes type I, gastritis, autoimmune atrophic gastritis, autoimmune hepatitis, Hashimoto's thyroiditis, thyreoiditis, multiple sclerosis, myasthenia gravis, autoimmune haemolytic anemia, Addison's disease, scleroderma, Goodpasture's syndrome, Guillain-Barre syndrome, Graves' disease, glomerulonephritis, psoriasis, pemphigus vulgaris, pemphigoid, vitiligo, idiopathic leukopenia, Sjogren's syndrome or Wegener's granulomatosis; (iii) an inflammatory disease due to organ transplantation; (iv) a bone marrow transplantation; or (v) a disease due to exogenously administered self or exogenously administered non-autologous recombinant polypeptide which method comprises administering to a being in need of such a treatment a suitable amount of a pharmaceutical composition comprising at least one Treg cell activator.

The present invention additionally, provides for a use of a Treg cell activator according to the present invention for reducing and/or preventing an unwanted immune reaction due to a exogenously administered self or exogenously administered non-autologous recombinant polypeptide and provides for a method for reducing or preventing an unwanted immune reaction comprising: (a) adding a sufficient amount of at least one Treg cell activator according to the present invention to a non-human animal, preferably a non-human primate.

In a further embodiment the present invention provides for a test system for determining whether a substance is a Treg cell activator according to the present invention comprising at least a) a Treg cell and b) a peptide spanning at least the epitope as set forth in SEQ ID NO.: 1

In a preferred test system of the present invention a peptide of b) is selected from a group consisting of an isolated peptide spanning amino acid No. 26 to 458 of SEQ ID NO.: 2, amino acid No. 26 to 419 of SEQ ID NO.: 2, amino acid No. 26 to 207 of SEQ ID NO.: 2, amino acid No. 26 to 131 of SEQ ID NO.: 2, and amino acid No. 46 to 89 of SEQ ID NO.: 2. or the peptide used is an isolated peptide spanning amino acid No. 1 to 31 of SEQ ID NO.: 1 and having additional up-stream and/or downstream amino acids with the prerequisite that the additional amino acids do not hinder binding of a substance to the amino acid stretch as set forth in SEQ ID No.:1. Said additional up-stream amino acid or amino acid stretch is preferably selected from a group consisting of the amino acid or amino acid stretch as set forth in SEQ ID NO.: 2 at position 53, at position 52-53, at position 51-53, at position 50-53, at position 49-53, at position 48-53, at position 47-53, at position 46-53, at position 45-53, at position 44-53, at position 43-53, at position 42-53, at position 41-53, at position 40-53, at position 39-53, at position 38-53, at position 37-53, at position 36-53, at position 35-53, at position 34-53, at position 33-53, at position 32-53, at position 31-53, at position 30-53, at position 29-53, at position 28-53, at position 27-53, at position 26-53, at position 25-53, at position 24-53, at position 23-53, at position 22-53, at position 21-53, at position 20-53, at position 19-53, at position 18-53, at position 17-53, at position 16-53, at position 15-53, at position 14-53, at position 13-53, at position 12-53, at position 11-53, at position 10-53, at position 9-53, at position 8-53, at position 7-53, at position 6-53, at position 5-53, at position 4-53, at position 3-53, at position 2-53, and at position 1-53. A more preferred peptide does additionally comprise downstream one or more amino acids as set forth in SEQ ID NO.: 2 at position 85, or at position 85 to n, wherein n is an integer between 86-458, i.e. position 85 to 86, 85 to 87, 85 to 88, 85 to 89, 85 to 90, 85 to 91, 85 to 92, 85 to 93, 85 to 94, 85 to 95, 85 to 96, 85 to 97, 85 to 98, 85 to 99, 85 to 100, 85 to 101, 85 to 102, 85 to 103, 85 to 104, 85 to 105, 85 to 106, 85 to 107, 85 to 108, 85 to 109, 85 to 110, 85 to 111, 85 to 112, 85 to 113, 85 to 114, 85 to 115, 85 to 116, 85 to 117, 85 to 118, 85 to 119, 85 to 120, 85 to 121, 85 to 122, 85 to 123, 85 to 124, 85 to 125, 85 to 126, 85 to 127, 85 to 128, 85 to 129, 85 to 130, 85 to 131, 85 to 132, 85 to 133, 85 to 134, 85 to 135, 85 to 136, 85 to 137, 85 to 138, 85 to 139, 85 to 140, 85 to 141, 85 to 142, 85 to 143, 85 to 144, 85 to 145, 85 to 146, 85 to 147, 85 to 148, 85 to 149, 85 to 150, 85 to 151, 85 to 152, 85 to 153, 85 to 154, 85 to 155, 85 to 156, 85 to 157, 85 to 158, 85 to 159, 85 to 160, 85 to 161, 85 to 162, 85 to 163, 85 to 164, 85 to 165, 85 to 166, 85 to 167, 85 to 168, 85 to 169, 85 to 170, 85 to 171, 85 to 172, 85 to 173, 85 to 174, 85 to 175, 85 to 176, 85 to 177, 85 to 178, 85 to 179, 85 to 180, 85 to 181, 85 to 182, 85 to 183, 85 to 184, 85 to 185, 85 to 186, 85 to 187, 85 to 188, 85 to 189, 85 to 190, 85 to 191, 85 to 192, 85 to 193, 85 to 194, 85 to 195, 85 to 196, 85 to 197, 85 to 198, 85 to 199, 85 to 200, 85 to 201, 85 to 202, 85 to 203, 85 to 204, 85 to 205, 85 to 206, 85 to 207, 85 to 208, 85 to 209, 85 to 210, 85 to 211, 85 to 212, 85 to 213, 85 to 214, 85 to 215, 85 to 216, 85 to 217, 85 to 218, 85 to 219, 85 to 220, 85 to 221, 85 to 222, 85 to 223, 85 to 224, 85 to 225, 85 to 226, 85 to 227, 85 to 228, 85 to 229, 85 to 230, 85 to 231, 85 to 232, 85 to 233, 85 to 234, 85 to 235, 85 to 236, 85 to 237, 85 to 238, 85 to 239, 85 to 240, 85 to 241, 85 to 242, 85 to 243, 85 to 244, 85 to 245, 85 to 246, 85 to 247, 85 to 248, 85 to 249, 85 to 250, 85 to 251, 85 to 252, 85 to 253, 85 to 254, 85 to 255, 85 to 256, 85 to 257, 85 to 258, 85 to 259, 85 to 260, 85 to 261, 85 to 262, 85 to 263, 85 to 264, 85 to 265, 85 to 266, 85 to 267, 85 to 268, 85 to 269, 85 to 270, 85 to 271, 85 to 272, 85 to 273, 85 to 274, 85 to 275, 85 to 276, 85 to 277, 85 to 278, 85 to 279, 85 to 280, 85 to 281, 85 to 282, 85 to 283, 85 to 284, 85 to 285, 85 to 286, 85 to 287, 85 to 288, 85 to 289, 85 to 290, 85 to 291, 85 to 292, 85 to 293, 85 to 294, 85 to 295, 85 to 296, 85 to 297, 85 to 298, 85 to 299, 85 to 300, 85 to 301, 85 to 302, 85 to 303, 85 to 304, 85 to 305, 85 to 306, 85 to 307, 85 to 308, 85 to 309, 85 to 310, 85 to 311, 85 to 312, 85 to 313, 85 to 314, 85 to 315, 85 to 316, 85 to 317, 85 to 318, 85 to 319, 85 to 320, 85 to 321, 85 to 322, 85 to 323, 85 to 324, 85 to 325, 85 to 326, 85 to 327, 85 to 328, 85 to 329, 85 to 330, 85 to 331, 85 to 332, 85 to 333, 85 to 334, 85 to 335, 85 to 336, 85 to 337, 85 to 338, 85 to 339, 85 to 340, 85 to 341, 85 to 342, 85 to 343, 85 to 344, 85 to 345, 85 to 346, 85 to 347, 85 to 348, 85 to 349, 85 to 350, 85 to 351, 85 to 352, 85 to 353, 85 to 354, 85 to 355, 85 to 356, 85 to 357, 85 to 358, 85 to 359, 85 to 360, 85 to 361, 85 to 362, 85 to 363, 85 to 364, 85 to 365, 85 to 366, 85 to 367, 85 to 368, 85 to 369, 85 to 370, 85 to 371, 85 to 372, 85 to 373, 85 to 374, 85 to 375, 85 to 376, 85 to 377, 85 to 378, 85 to 379, 85 to 380, 85 to 381, 85 to 382, 85 to 383, 85 to 384, 85 to 385, 85 to 386, 85 to 387, 85 to 388, 85 to 389, 85 to 390, 85 to 391, 85 to 392, 85 to 393, 85 to 394, 85 to 395, 85 to 396, 85 to 397, 85 to 398, 85 to 399, 85 to 400, 85 to 401, 85 to 402, 85 to 403, 85 to 404, 85 to 405, 85 to 406, 85 to 407, 85 to 408, 85 to 409, 85 to 410, 85 to 411, 85 to 412, 85 to 413, 85 to 414, 85 to 415, 85 to 416, 85 to 417, 85 to 418, 85 to 419, 85 to 420, 85 to 421, 85 to 422, 85 to 423, 85 to 424, 85 to 425, 85 to 426, 85 to 427, 85 to 428, 85 to 429, 85 to 430, 85 to 431, 85 to 432, 85 to 433, 85 to 434, 85 to 435, 85 to 436, 85 to 437, 85 to 438, 85 to 439, 85 to 440, 85 to 441, 85 to 442, 85 to 443, 85 to 444, 85 to 445, 85 to 446, 85 to 447, 85 to 448, 85 to 449, 85 to 450, 85 to 451, 85 to 452, 85 to 453, 85 to 454, 85 to 455, 85 to 456, 85 to 457, or 85 to 458.

The following examples are meant to illustrate the present invention, however, shall not be construed as limitation. However, the Examples describe most preferred embodiments of the invention.

EXAMPLES (1) CD4/HIV-1 gp120 Competition Assay for Determining Whether a Substance can Bind at Least to a Peptide Spanning Epitope as Set Fourth in SEQ ID NO.:1

96 well assay plates (Nunc, Germany) are coated overnight at 4° C. with CD4 (sCD4, Immunodiagnostics, USA) 100 ng per well in PBS, pH 7.4. Coated plates are saturated with PBS/3% BSA buffer and washed three times. To determine binding of a test substance sample is added for 1 hour in different concentrations. No test substance is added to control wells. After washing three times HIV-1 gp120-peroxidase conjugate (Immunodiagnostics, USA) is added to the plate for 1 h. Unbound HIV-1 gp120-peroxidase conjugate is removed by washing three times After washing, 3,3,5,5-tetramethylbenzidine chromogen substrate (Pierce, USA) for peroxidase is added and the optical density is read at 450 nm. A substance which interacts with the CD4 HIV-1 gp120-binding site will block the binding of labeled HIV-1 gp120 and is identifiable by a reduced signal compared to the controls.

(2) Assay for Determining Whether E.G. HIV-1 gp120 or a Substance which can Interfere with HIV-1 gp120-Binding to a $CD4^+CD25^+$ Treg can Activate a $CD4^+CD25^+$ Treg and Therewith can be Useful in the Treatment an Autoimmune Disease (E.G. Inflammatory Bowel Disease, Multiple Sclerosis, Rheumatoid Arthritis, Psoriasis, Diabetes Type I, Lupus Erythematosus, Phemphigus Vulgaris, Thyreoiditis), Other Diseases with Autoimmune Aspects in their Pathogenesis Such as Vitiligo, Atopic Dermatitis, an Allergy (E.G. Allergic Rhinitis), Asthma (E.G. Allergic Asthma), GVHD (Graft-Versus-Host Disease), Graft Resection (2.1) Method for Isolation of Cells (2.1.1) Isolation of PBMC The isolation procedure starts with PBMC (peripheral blood mononuclear cells) isolated by standard density gradient centrifugation from normal buffy coat preparations of healthy volunteers. Alternatively, PBMC isolated from whole peripheral blood or leukapheresis products can be used.

Blood from buffy coats is diluted 1:1 with PBS (phosphate buffered saline) containing 0.2% Liquemine (Sodium-Heparin) and 2 mM EDTA at room temperature. The diluted blood is thoroughly pipetted onto prepared Ficoll layers (30 ml diluted blood per 15 ml Ficoll layer per 50 ml tube) and centrifuged for 15 min. (minute) at 200×g (with brake on) at room temperature. 8-10 ml of the upper fluid are carefully removed and the tubes centrifuged at 450×g for 15 min. at room temperature (with brake off). PBMC are collected from the interphase of each gradient, washed three times with 50 ml PBS/1 mM EDTA separately, than pooled and wash two more times. Finally, PBMC are re-diluted in X-VIVO-15 (Cambrex, Verviers, Belgium) in cell culture medium and counted.

(2.1.2) Isolation of $CD4^+$ T Helper Cells

For determining suppressive activity of Treg cells highly purified cell populations are needed. Therefore, antibody-coated magnetic beads are used (Miltenyi, Germany and or Dynal, Norway). Magnetic beads in this context are paramagnetic particles that are coupled to specific monoclonal antibodies. They are used to magnetically label the target cell population. The antibody-coated magnetic beads bind to the target cells. This labeled cell fraction is retained by magnetic force and can be recovered subsequently highly purified (positive selection). Before positive isolation of $CD4^+CD25^-$ T helper cells PBMC are washed two times with 50 ml washing buffer according to the manufacturer's instructions (Miltenyi Germany). For isolation of $CD4^+$ T cells, CD4 microbeads (Miltenyi Germany, 2-4 μL microbeads/$10^7$ PBMC) are used according to the manufacturer's instructions. The $CD4^+$ fraction is isolated using a MACS separator (Miltenyi) according to the instructions of the manufacturer. MACS separator retains magnetic bead-labeled cells by magnetic force. Contaminating $CD4^+CD25^+$ Treg cells are depleted in a second step by using CD25 Dynabeads, (Dynal, Norway) according to the instructions of the manufacturer (details see 2.1.4) using (0.5 beads/cell). This depletion procedure results in highly purified $CD4^+CD25^-$ T helper cells (negative selection).

To circumvent CD4 antibodies binding to $CD4^+$ cells (to avoid CD4-dependent pre-activation) in the isolation procedure of $CD4^+$ T cells, alternatively untouched $CD4^+$ T helper cells are generated by using the negative isolation kit (Miltenyi Germany) according to the manufacturer's instructions. Before negative isolation of $CD4^+$ T helper cells PBMC are washed two times with 50 ml washing buffer according to the manufacturer's instructions (Miltenyi Germany). For isolation of $CD4^+$ T helper cells, PBMC are incubated with a cocktail of biotinylated CD45RO, CD8, CD14, CD16, CD19, CD56, CD36, CD123, anti-TCRγ/δ, and CD235a antibodies. These cells are subsequently magnetically labeled with Anti-Biotin Microbeads for depletion. The $CD4^+$ fraction is isolated using a MACS separator (Miltenyi) according to the instructions of the manufacturer. MACS separator retains magnetic bead-labeled cells by magnetic force. Contaminating $CD4^+CD25^+$ Treg cells are depleted in a second step by using CD25 Dynabeads, (Dynal, Norway) according to the instructions of the manufacturer (details see 2.1.4) using 0.5 beads/cell.

(2.1.3) Isolation of $CD8^+$ T Effector Cells

Before positive isolation of $CD8^+$ T effector cells PBMC are washed two times with 50 ml washing buffer according to the manufacturer's instructions (Miltenyi Germany). For isolation of $CD8^+CD25^-$ T-cells, CD8 microbeads (Miltenyi Germany, 2-4 μL microbeads/$10^7$ PBMC) are used according to the manufacturer's instructions. The $CD8^+$ fraction is isolated using a MACS separator (Miltenyi) according to the instructions of the manufacturer. Contaminating $CD8^+CD25^+$ T cells are depleted in a second step by using CD25 Dynabeads, (Dynal, Norway) according to the instructions of the manufacturer (details see 2.1.4) using (0.5 beads/cell). This depletion procedure results in highly purified $CD8^+CD25^-$ T effector cells (negative selection).

(2.1.4) Isolation of $CD4^+CD25^+$ Treg Cells

For Isolation of $CD4^+CD25^+$ Treg cells positive and negative selection is combined. PBMC are washed with washing buffer according to the manufacturer's instructions (Miltenyi Germany) and subsequently incubated with CD25 microbeads (2 μL microbeads/$10^7$ PBMC) for 20 min. at 4° C. in isolation buffer ($1\times10^8$/ml) according to the manufacturer's instructions. Afterwards, the cells are washed two times in PBS. The $CD25^+$ fraction is isolated using a MACS separator (Miltenyi) according to the instructions of the manufacturer. The positively selected $CD25^+$ fraction contains 65-80% $CD4^+$ T cells and 20-35% contaminating $CD19^+$ B cells, $CD8^+$ T cells, and few $CD14^+$ monocytes. The contaminating cells are depleted with Dynabeads (Dynal, Norway). The following amounts of beads are used: CD19 Dynabeads: 2 beads/cell, CD8 Dynabeads: 3 beads/cell, CD14 Dynabeads: 1 bead/cell. Collected Dynabeads are washed two times in 15-ml tubes with depletion buffer using the magnetic particle concentrator (Dynal) according to the manufacturer's instructions. The $CD25^+$ PBMC fraction ($5\times10^7$/ml) is added in depletion buffer and incubated for 20 min. at 4° C. on a shaker (sample mixer, Dynal). Contaminating cells are depleted according to the manufacturer's instructions by the use of the magnetic particle concentrator. For higher purity of $CD4^+CD25^+$ Treg cells Dynabeads depletion is repeated once (>98% after two rounds of depletion).

(2.1.5) Generation of Monocyte-Derived Dendritic Cells

Dendritic cells (DC) are generated from buffy coats of healthy volunteers. PBMC (2.1.6) are plated in 6-well tissue culture plates at a density of $15\times10^6$ cells/well in 3 ml X-VIVO-15 (Cambrex, Verviers, Belgium) plus 1.5% heat-inactivated autologous plasma containing 800 U/ml GM-CSF (Leukomax; Novartis, Basel, Switzerland) and 1,000 U/ml IL-4 (Strathmann Biotec, Hamburg, Germany). Cultures are fed every other day (days 2, 4 and 6) by removing 1 ml of the medium and adding back 1 ml fresh medium with cytokines. On day 7, non-adherent cells were harvested and transferred to new 6 well plates and cultured further on in the presence of 10 ng/ml IL-1β, 10 ng/ml TNF-α, 1,000 U/ml IL-6 (all from Strathmann, Biotech, Germany) and 1 μg/ml $PGE_2$ (Pharmacia-Upjohn, Uppsala, Sweden). Mature $CD83^+$ DC are harvested at day 9 of culture.

(2.1.6) Isolation of CD3-Depleted PBMC

T cells are depleted from PBMC with CD3 Dynabeads (Dynal, Norway) by using 0.5 beads/cell. Collected Dynabeads are washed two times in 15 ml tubes with depletion buffer using the magnetic particle concentrator (Dynal) according to the manufacturer's instructions. PBMC ($5\times10^7$/ml) are added in depletion buffer and incubated for 20 min. at 4° C. on a shaker (sample mixer, Dynal). $CD3^+$ cells are depleted according to the manufacturer's instructions by the use of the magnetic particle concentrator resulting in a purity of >98% $CD3^-$ PBMC.

(2.1.7) Isolation of Human CD25-Depleted PBMC

PBMC are isolated according to (2.1.1). CD25-expressing regulatory T cells in the PBMC preparation are depleted with CD25 Dynabeads (Dynal, Norway) according to the instructions of the manufacturer (details see 2.1.4) by using 0.5 beads/cell. Collected Dynabeads are washed two times in 15-ml tubes with depletion buffer using the magnetic particle concentrator (Dynal) according to the manufacturer's instructions. PBMC ($5\times10^7$/ml) are added in depletion buffer and incubated for 20 min. at 4° C. on a shaker (sample mixer, Dynal). $CD25^+$ cells are depleted according to the manufacturer's instructions by the use of the magnetic particle concentrator resulting in a purity of >99% CD25-negative PBMC.

(2.2) Method for Testing Suppressive Activity of $CD4^+CD25^+$ Treg Cells (2.2.1) Coculture Suppression Assay A: Mixed Leukocyte Reaction (MLR)

Cocultures of $CD4^+$ T helper cells or $CD8^+$ T effector cells with $CD4^+CD25^+$ Treg cells and allogeneic DC have to be performed to analyze the suppressive activity of $CD4^+CD25^+$ Treg cells on $CD4^+$ T helper cells or $CD8^+$ T effector cells. Therefore, $1\times10^5$/well $CD4^+$ T helper cells (2.1.2) or $CD8^+$ T effector cells (2.1.3) are cocultured with different numbers of $CD4^+CD25^+$ Treg cells (2.1.4; ratio 1:1 to 1:4) and $1\times10^4$/well DC in 96 well flat bottom culture plates in X-VIVO 15 (Cambrex, Verviers, Belgium) in the presence or absence of a CD4-binding compound e.g. HIV-1 gp120 (0.1-10 μg/ml). Mature dendritic cells (DC) generated as described (2.1.5) are from the same donor as $CD4^+CD25^+$ Treg cells (syngenic) but allogeneic to the $CD4^+$ T helper cells or $CD8^+$ T effector cells are used for T cell stimulation. In this assay, only $CD4^+$ T helper cells or $CD8^+$ T effector cells are activated by the allogeneic DC (MLR) resulting in a strong proliferation of the T cell subset. Non-activated $CD4^+CD25^+$ Treg cells did not suppress this proliferation in absence of a Treg cell activating compound. A functional activation of $CD4^+CD25^+$ Treg cells by a CD4-binding compound resulted in a reduced proliferation of $CD4^+$ T helper cells or $CD8^+$ T effector cells.

Proliferation is determined after 4 days of culture by adding 37 kBq 3H-Thymindine (3H-Tdr) for additional 16 h.

(2.2.2) Coculture Suppression Assay B: Stimulation of $CD8^+$ T Effector Cells with Allogeneic PBMC and $CD4^+CD25^+$ Treg Cells from the Same Healthy Volunteer.

In order to study the influence of a substance, e.g. HIV-1 gp120 which can bind at least to the epitope given in SEQ ID NO.:1 exclusively on the suppressive function of $CD4^+CD25^+$ Treg cells, we developed a co-culture assay which contained $CD8^+$ T cells as effectors to exclude any influence of this substance on the latter ($CD8^+$ T cells don't express CD4). In this setting, activation of alloreactive $CD8^+$ T effector cells is only suppressed by activated $CD4^+CD25^+$ Treg cells such as upon additional anti-CD3 mAb stimulation (positive control). To evaluate the influence of e.g. HIV-1 gp120 on the function of $CD4^+CD25^+$ Treg cells, isolated $CD4^+CD25^+$ Treg cells (2.1.4) are co-cultured with syngenic, T cell-depleted and irradiated (50 Gy) PBMC (2.1.6) and allogeneic $CD8^+$ T effector cells (2.1.3) in presence of varying concentrations (0.1-10 μg/ml) of different HIV-1 gp120 preparations. Briefly, $1\times10^5$ $CD4^+CD25^+$ Treg cells are incubated with $3\times10^5$ syngenic T cell-depleted PBMC in the presence or absence of varying amounts of HIV-1 gp120. Stimulation with 0.5 μg/ml anti-CD3 monoclonal antibody (OKT-3, ebioscience, USA) serves as positive control. No additional stimulation represents negative control. Either immediately or 24 h later, $1\times10^5$ allogeneic $CD8^+$ T effector cells are added to the cultures and proliferation is determined after additional 72 h by $^3$H-Tdr incorporation (37 kBq/well). Functional activation of $CD4^+CD25^+$ Treg cells via interaction with the epitope as set forth in SEQ ID NO:1 result in suppressed proliferation of $CD8^+$ T effector cells and therewith identifies a substance as a Treg cell activator (Data see FIG. 1).

To show in parallel whether a substance can interfere with HIV-1 gp120 binding to CD4 epitope of a $CD4^+CD25^+$ Treg cell, CD4 is added in different concentrations (0.1-10 μg/ml) to isolated $CD4^+CD25^+$ Treg cells (2.1.4) cocultured with syngenic T cell-depleted PBMC (2.1.6) and allogeneic $CD8^+$ T effector cells (2.1.3) in the presence of varying amounts of the substance. Enhanced proliferation of $CD8^+$ effector cells resembles competitive binding to CD4 and blocked activation of a Treg cell via interaction with the epitope as set forth in SEQ ID NO:1. All cultures are performed in serum free X-VIVO-15 (Cambrex, Verviers, Belgium).

Alternatively to irradiation-induced inactivation and block of proliferation PBMC can be treated with Mitomycin C (Sigma, Germany). Briefly, $3\times10^7$ PBMC are incubated in 3 ml MEM/10% FCS/180 μg Mitomycin C for 30 min at 37° C. Afterwards cells are washed 5× using MEM/10% FCS. Subsequently cells are subjected to the assay.

(2.2.3) Coculture Suppression Assay C: Stimulation of T Cells in Presence of Pre-Activated $CD4^+CD25^+$ Treg Cells and Allogeneic PBMC To evaluate the direct Treg cell activating potential of a compound in the absence of antigen-presenting cells such as PBMC, isolated $CD4^+CD25^+$ Treg cells (according to 2.1.4) are pre-cultured in X-VIVO-15 for 16-48 h alone, in presence of 0.5 μg/ml anti-CD3 monoclonal antibody (OKT-3) as positive control, or in presence of different concentrations of HIV-1 gp120. Afterwards, cells are washed intensively and added to cocultures of syngenic, irradiated (50 Gy) PBMC and allogeneic $CD4^+$ T helper cells or $CD8^+$ T effector cells. Proliferation is determined after additional 72 h by $^3$H-Tdr incorporation (37 kBq/well). Functional activation of $CD4^+$ $CD25^+$ Treg cells via interaction with the epitope as set forth in SEQ ID NO:1 result in suppressed proliferation of $CD4^+$ T helper cells or $CD8^+$ T effector cells and therewith identifies a substance as a Treg cell activator.

A reduced incorporated radioactivity resembles suppressed proliferation and identifies $CD8^+$ inhibition and therewith identifies a substance to activate a Treg cell via interaction with the epitope as set forth in SEQ ID NO:1.

(2.3.) Method for Readout of Suppressive Activity of $CD4^+$ $CD25^+$ Treg Cells (2.3.1) Analysis of Proliferation After 3-4 days of incubation of cells in assays provided under (2.2.1), (2.2.2) and (2.2.3) T cell proliferation is measured. For additional 16 h, cells are pulsed with $^3$H-Tdr (37 kBq/well, MB Biomedicals), and incorporated radioactivity is measured by using a liquid scintillation counter (Betaplate, Wallac/PerkinElmer). In the absence of a Treg cell activating compound, resting Treg cells cannot inhibit the proliferation of $CD4^+$ T helper cells or $CD8^+$ T effector cells (negative control). In contrast, in presence of an activating CD4-binding compound or anti-CD3 monoclonal antibody (positive control) the proliferation of $CD4^+$ T helper cells or $CD8^+$ T effector cells is suppressed by $CD4^+CD25^+$ Treg cells. A reduced incorporated radioactivity resembles suppressed proliferation and identifies $CD4^+$ T helper cell or $CD8^+$ T effector cell inhibition and therewith identifies that a $CD4^+$ $CD25^+$ Treg cell has been activated.

For some experiments the proliferation of either $CD4^+$ $CD25^+$ Treg cells, $CD4^+$ T helper cells or $CD8^+$ T effector cells is selectively followed by flow cytometry after labeling of these population with Vibrant CFDA SE Cell Tracer Kit (Invitrogen Life Technologies, San Diego, USA) according to the manufacturer's protocol. For CFDA labeling, T cells ($1\times10^7$ cells/ml) are incubated in PBS with 1 μM CFDA Vibrant CFDA SE Cell Tracer Kit (Invitrogen Life Technologies, San Diego, USA) at 37° C. for 30 min. Thereafter, cells are washed with X-VIVO-15 and incubated for 30 min. at 37° C. in the dark. After an additional wash the cells are counted and added to the cocultures. In addition, proliferation of cells is measured by flow cytometry after 4-6 days of culture.

(2.3.2) Analysis of Cytokine Production

Activated Treg cells not only inhibit the proliferation of cocultured $CD4^+$ T helper cells or $CD8^+$ T effector cells, they suppress also the cytokine synthesis of these T cells. Therefore, detection of cytokines produced by cocultured T cells is an alternative method to analyze the Treg cell activating potential of a reagent. In this assay, isolated $CD4^+CD25^+$ Treg cells (according to 2.1.4), syngenic CD3-depleted PBMC (according to 2.1.6) and allogeneic $CD8^+$ T effector cells (according to 2.1.3) are cocultured as described (2.2) before. After 7 days, alloreactive $CD8^+$ T effector cells are polyclonal restimulated with 2.4 μg/ml phytohemagglutinin (PHA, Sigma, Germany) and 1 ng/ml PMA for 5 h in presence of monensin (BD GolgiStop™, BD Biosciences Pharmingen 1.3 μM). Thereafter, cells are collected, washed with PBS, fixed and permeabilized according to the manufacturer's instruction (perm/fix solution, BD PharMingen, Germany) and stained with 0.5 μg/test of a cytokine-specific monoclonal antibody (anti-IFN-γ, anti-IL-2, anti-TNF-α, all from BD PharMingen). Subsequently, production of cytokines by $CD4^+$ T helper cells or $CD8^+$ T effector cells is analyzed by flow cytometry. In the absence of a Treg cell activating compound Treg cells cannot inhibit the cytokine production of $CD4^+$ T helper cells or $CD8^+$ T effector cells (negative control). In contrast, in presence of an activating CD4-binding compound or anti-CD3 monoclonal antibodies (positive control) the cytokine production of $CD4^+$ T helper cells or $CD8^+$ T effector cells is suppressed by functional activated Treg cells. A reduced cytokine production identifies inhibition and therewith identifies that a $CD4^+CD25^+$ Treg cell has been activated.

(2.3.3) Analysis of CD25 Expression

Activated Treg cells inhibit the ability of $CD8^+$ T effector cells and $CD4^+$ T helper cells to express the α-chain of the IL-2 receptor, CD25. Therefore, the analysis of CD25 expression by flow cytometry is an additional method to evaluate the Treg cell activating potential of a reagent. In this assay, isolated $CD4^+CD25^+$ Treg cells (according to 2.1.4) and syngenic CD3-depleted PBMC (according to 2.1.6) are cocultured with allogeneic $CD8^+$ T effector cells or allogeneic $CD4^+$ T helper cells (according to 2.1.3, 2.1.2 and 2.2.1, 2.2.2 and 2.2.3). After 7 days, alloreactive $CD8^+$ T effector cells or allogeneic $CD4^+$ T helper cells are stimulated with allogeneic PBMC from the same donor or DC as used in primary culture and expression of CD25 on alloreactive $CD8^+$ T effector or allogeneic $CD4^+$ T helper cells are analyzed 24 h thereafter by flow cytometry. Activation of Treg cells by the test compound results directly in an inhibited CD25 expression on the re-stimulated $CD8^+$ T effector cells or $CD4^+$ T helper cells. In the absence of a Treg cell activating compound, Treg cells cannot inhibit the CD25 expression on re-stimulated $CD8^+$ T effector cells or $CD4^+$ T helper cells (negative control). In contrast, in presence of an activating reagent or an anti-CD3 monoclonal antibody (positive control) the CD25 expression of $CD8^+$ T effector cells or $CD4^+$ T helper cells is suppressed by Treg cells. A reduced CD25 expression identifies inhibition and therewith identifies that a $CD4^+CD25^+$ Treg cell has been activated.

(2.3.4) Analysis of Cyclic AMP Production

Stimulation of Treg cells results in strong increase of cytosolic (i.e intracellular) cAMP. Therefore, the analysis of cAMP in Treg cells is an additional method to determine whether a substance which can interfere with HIV-1 gp120 binding to CD4 epitope of a CD4-positive cell can activate a Treg cell. In this assay freshly isolated $CD4^+CD25^+$ Treg cells (according to 2.1.4) ($1\times10^5$-$1\times10^6$/well) are incubated with anti-CD3 monoclonal antibody (OKT-3; 0.5 μg/ml) or HIV-1 gp120 (0.1-10 μg/ml; Protein Science Corp., Meriden, Conn., USA) or left untreated for 16 hours. To assess cytosolic cAMP-concentrations a cAMP-specific ELISA (Parameter™ Cyclic AMP Assay, Cat. No. KGE002; R&D Systems, Wiesbaden, Germany) is applied. Treg cells are washed three times in ice-cold PBS and subsequently lysed ($1\times10^7$/ml) using lysis buffer supplied by the manufacturer and applied to the ELISA according to the manufacturer's recommendations.

Activation of Treg cells by the test compound results directly in an increase of cytosolic cAMP. In the absence of a Treg cell activating compound no increase of cAMP in $CD4^+$ $CD25^+$ Treg cells is detected (negative control). In contrast, in presence of an activating CD4-binding compound or an anti-CD3 monoclonal antibody (positive control) $CD4^+CD25^+$ Treg cell show a strong increase of cytosolic cAMP. An increase of cytosolic cAMP identifies that a $CD4^+CD25^+$ Treg cell has been activated. Data see FIG. 2.

Alternatively, additional analysis of assay supernatant cAMP concentration and use of phoshodiesterase inhibitors e.g. Roflumilast (1-50 μM) enhance the cAMP signal in the assay.

(3) In Vivo Assay for Determining Whether HIV-1 gp120 or a Substance which can Interfere with HIV-1 gp120-Binding to a $CD4^+CD25^+$ Treg can Activate a $CD4^+CD25^+$ Treg in a Disease-Related Model and Therewith can be Useful in the Treatment of an Autoimmune Disease (e.g. Inflammatory Bowel Disease, Multiple Sclerosis, Rheumatoid Arthritis, Psoriasis, Diabetes Type I, Lupus Erythematosus, Phemphigus Vulgaris, Thyreoiditis), Other Diseases with Autoimmune Aspects in their Pathogenesis such as Vitiligo, Atopic Dermatitis, an Allergy (e.g. Allergic Rhinitis), Asthma (e.g. Allergic Asthma), GVHD (Graft-Versus-Host Disease), Graft Resection (3.1) Method for Induction of GVHD by Transfer of Human PBMC into NOD-Scid Mice and Measurement of Disease Severity.

NOD-Scid mice, non-obese diabetic/severe combined immunodeficient mice (mutant allele: $Prkdc^{scid}$, strain: NOD.CB17-$Prkdc^{scid}$, (Shultz et al 1995)) from the Central Laboratory Animal Facility of the University of Mainz (also purchasable from The Jackson Laboratory via Charles River Laboratories, Germany) are used as an animal model for transfer of peripheral human immune cells and thus for the in vivo analysis of immuno-regulatory interactions (Hesselton et al. 1995). Human peripheral blood mononuclear cells (PBMC) transferred into NOD-Scid mice induce an accelerating age-dependent graft-versus-host disease (GVHD). While the number of cells transferred determines the onset of this disease, the co-transfer of human Tregs can gradually delay or prevent the disease. This model system further allows the study of human Treg function. To induce a GVHD NOD-Scid mice at the age of three to six days after birth are intraperitoneally injected with $1\times10^7$ to $3\times10^7$ human PBMC (isolation of human PBMC according to 2.1.1). GVHD is induced by immunological (xenogenic) activation of human effector T cells in the PBMC fraction injected into the mice. NOD-Scid mice, however, are not able to react against the grafted human PBMC. The human PBMC-induced disease is characterized by lack of weight increase and weight loss, decreased mobility, hunched posture, ruffled fur and organ inflammation in the treated animals (Kizilisik and Al-Sebayel 1997). Transfer of human PBMC results in growth arrest or weight loss within 30 to 40 days (depending on the number of cells transferred) after transfer compared to untreated mice. Lack of weight increase/weight loss is used as a parameter to score GVHD severity. Control mice did not receive any PBMC. Data see FIG. 3.

(3.2) Method for Induction of GVHD by Transfer of Human PBMC into Nod-Scid Mice and Prevention of Disease by Additional Transfer of Human Regulatory T Cells and Measurement of Disease Severity.

To prevent a GVHD disease in NOD-Scid mice at the age of three to six days after birth induced by intraperitoneally injection of $1\times10^7$ to $3\times10^7$ human PBMC (isolation of human PBMC according to 2.1.1) additional $2.5\times10^6$ human regulatory T cells (isolation of human regulatory T cells according to 2.1.4) are injected intraperitoneally (ratio Tregs to PBMC: 1:4). Co-transfer of human regulatory T cells along with human PBMC (enhancement of Treg ratio) results in prevention of development of GVHD and weight loss similar development as untreated mice. Lack of weight increase/weight loss is used as a parameter to score GVHD severity. Control mice did not receive any PBMC. Data see FIG. 3.

(3.3) Method for Induction of GVHD by Transfer of Human PBMC into Nod-Scid Mice and Prevention of Disease by Additional Administration of HIV-1 gp120 or a Substance which can Interfere with HIV-1 gp120-Binding and Measurement of Disease Severity.

To prevent a GVHD disease induced in NOD-Scid mice at the age of three to six days after birth induced by intraperitoneally injection of $1\times10^7$ to $3\times10^7$ human PBMC (isolation of human PBMC according to 2.1.1) HIV-1 gp120 or a substance which can interfere with HIV-1 gp120-binding is administered in addition to the injection of human PBMC. Administration of HIV-1 gp120 or a substance which can interfere with HIV-1 gp120-binding induces an activation of human regulatory T cells in the PBMC fraction resulting in prevention of organ inflammation and prevention of growth arrest/weight loss similar to mice treated with human PBMC and additional human regulatory T cells or untreated mice. Lack of weight increase/weight loss is used as a parameter to score GVHD severity. Control mice did not receive any PBMC. Data see FIG. 4.

(3.4) Method for Induction of GVHD by Transfer of Human PBMC into Nod-Scid Mice and to Demonstrate that Prevention of Disease by Administration of HIV-1 gp120 or a Substance which can Interfere with HIV-1 gp120-Binding is Mediated by Human Regulatory T Cells in the PBMC Fraction Injected into Nod-Scid Mice and Measurement of Disease Severity.

NOD-Scid mice at the age of three to six days after birth are intraperitoneally injected with $1\times10^7$ human CD25-depleted PBMC (isolation of human CD25-depleted PBMC according to 2.1.7). GVHD is induced by $1\times10^7$ human CD25-depleted PBMC at the same magnitude as by transfer of $1\times10^7$ human non CD25-depleted PBMC into NOD-Scid mice. (Data see FIG. 5 and FIG. 3 and FIG. 4) Mice receiving CD25-depleted PBMC and an additional administration of HIV gp120 are not protected from development of GVHD and weight loss. Prevention of GVHD by HIV gp120 or a substance which can interfere with HIV-1 gp120-binding depends on regulatory T cells. Lack of weight increase/weight loss is used as a parameter to score GVHD severity. Data see FIG. 5.

In order to study the influence of HIV-1 gp120 exclusively on the function of $CD4^+CD25^+$ Treg cells, we developed a coculture assay which contained $CD8^+$ T cells as effectors to exclude any influence of HIV-1 gp120 on the latter. Therefore, isolated $CD4^+CD25^+$ Treg cells are cocultured with T cell-depleted syngenic PBMC and allogeneic $CD8^+$ T effector cells. In this setting, proliferation of alloreactive $CD8^+$ T effector cells is only suppressed by activated $CD4^+CD25^+$ Treg cells such as upon additional anti-CD3 mAb stimulation or an activating HIV-1 gp120-mediated signal. (All HIV-1 gp120 proteins: Protein Sciences Corp. Meriden, USA)

$1\times10^5$ isolated $CD25^+$ Treg cells were incubated with $3\times10^5$ irradiated (50 Gy) syngenic T cell-depleted PBMC and $1\times10^5$ allogeneic $CD8^+$ T effector cells in presence/absence of different HIV-1 gp120 preparations, addition of 0.5 μg/ml anti-CD3 (OKT-3) served as positive control. Proliferation was determined by $^3$H-Tdr-Incorporation 4 days later.

Grey bars represent proliferation of $CD8^+$ T cells and inactivated syngenic CD3-depleted PBMC, white bars represent the proliferation of $CD4^+CD25^+$ Tregs and the black bars represent the proliferation of $CD8^+$ T cells co-cultured with $CD4^+CD25^+$ Tregs cells and inactivated syngenic CD3-depleted PBMC. Due to inactivation PBMC don't contribute to proliferation of the samples.

As can be seen by the low white bars, Tregs don't show a significant proliferation under all conditions (without additional stimulus, or anti-CD3, or HIV-1 gp120 MN, or HIV-1 gp120 LAV, or HIV-1 gp120 CM). $CD8^+$ T cells (grey bars) and $CD8^+$ T cells co-cultured with Treg cells (black bars) show the same magnitude of proliferation under the condition without additional stimulus representing the controls. Upon anti-CD3 stimulation $CD8^+$ T cells (grey bars) show strong increased proliferation but $CD8^+$ T cells co-cultured with Treg cells (black bars) show a reduced proliferation indicating suppressed proliferation of $CD8^+$ T cells by anti-CD3 activated and therefore suppressive Tregs. The effect is anti-CD3 dose-dependent. Upon stimulation with HIV-1 gp120 MN, or HIV-1 gp120 LAV, or HIV-1 gp120 CM $CD8^+$ T cells co-cultured with Treg cells (black bars) in contrast to $CD8^+$ T cells without Tregs (grey bars) reduced proliferation indicating HIV-1 gp120 activated Tregs. This demonstrates clearly that HIV-1 gp120 activates Tregs which subsequently exert suppressive activity on $CD8^+$ T cells by reducing their proliferation. The suppressive activity of Treg cells and therefore the reduced proliferation is HIV-1 gp120 dose-dependent.

Figure 1:
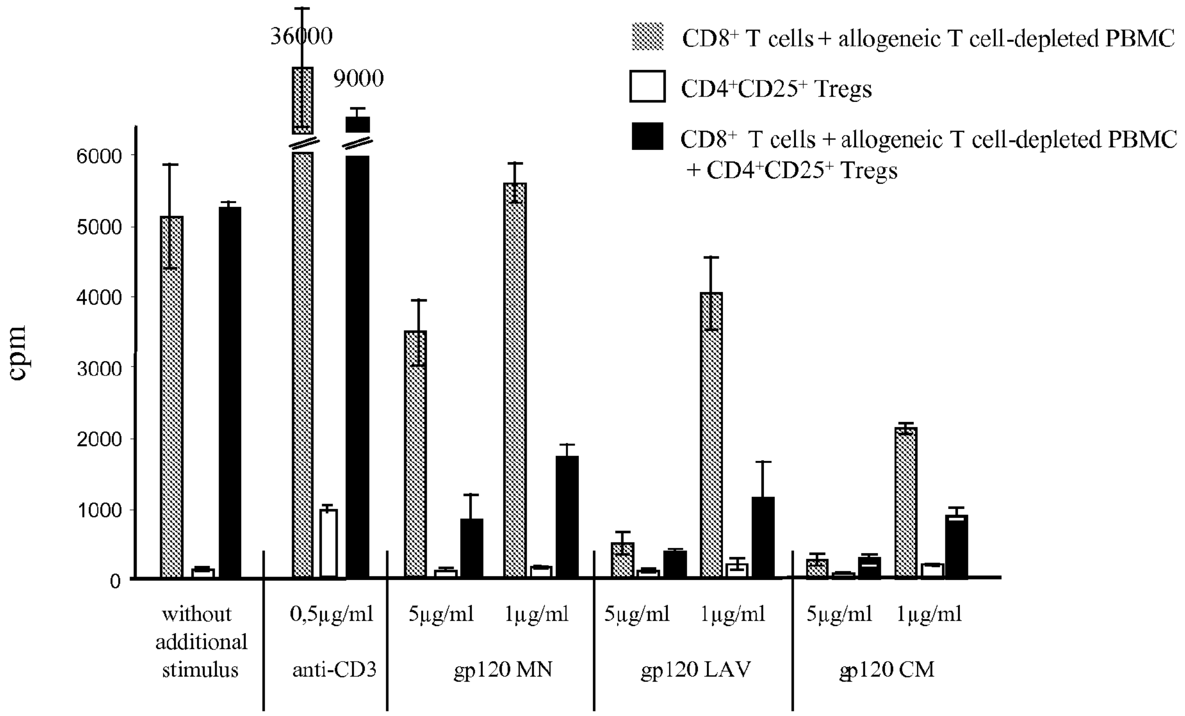
FIG. 1: HIV-1 gp120 Treatment Activates Human $CD4^+CD25^+$ Treg Cells
Figure 2:
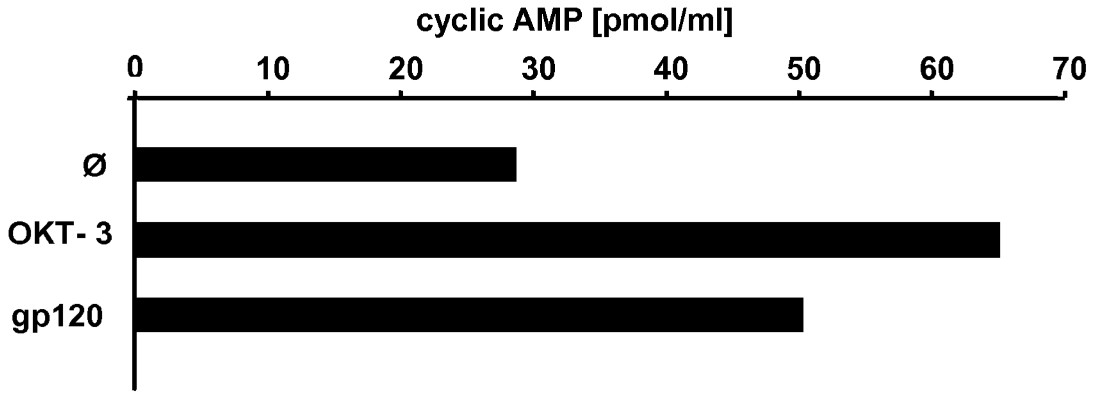

FIG. 2: Cyclic AMP Measurement in $CD4^+CD25^+$ Treg Cells

HIV-1 gp120 Treatment Augments Cytosolic Camp in Human $CD4^+CD25^+$ Treg Cells $CD4^+CD25^+$ regulatory T cells (CD25) are left untreated (ø) or stimulated with an anti-CD3 monoclonal Antibody (OKT-3; 1 μg/ml) or HIV-1 gp120 (1 μg/ml). Upon 16 hours of stimulation the $CD4^+CD25^+$ regulatory T cells are lysed ($1\times10^7$/ml) and the cytosolic cAMP concentration of $1\times10^6$ T cells is assessed using a cAMP-specific ELISA.

$CD4^+CD25^+$ regulatory T cells (CD25) are left untreated (ø) or stimulated with an anti-CD3 monoclonal Antibody (OKT-3; 1 μg/ml) or HIV-1 gp120 (1 μg/ml). Upon 16 hours of stimulation the $CD4^+CD25^+$ regulatory T cells are lysed ($1\times10^7$/ml) and the cytosolic cAMP concentration of $1\times10^6$ T cells is assessed using a cAMP-specific ELISA.

Bars represent the amount of cytosolic (intracellular) cyclic AMP (cAMP) in untreated Treg cells or Treg cells treated with different stimuli. The upper bar represent Tregs left untreated (ø) and shows the basal level of intracellular cAMP. Upon anti-CD3 stimulation (OKT-3) Tregs are activated and show an increase of intracellular cAMP compared to the untreated control (upper bar) as demonstrated with the second bar. Treatment of Tregs with HIV-1 gp120 also induces an increase of intracellular cAMP as demonstrated with the lower bar. This demonstrated that activation of Treg cells with different stimuli induces an increase of cytosolic cAMP which can be used as readout for activation.

Figure 3:
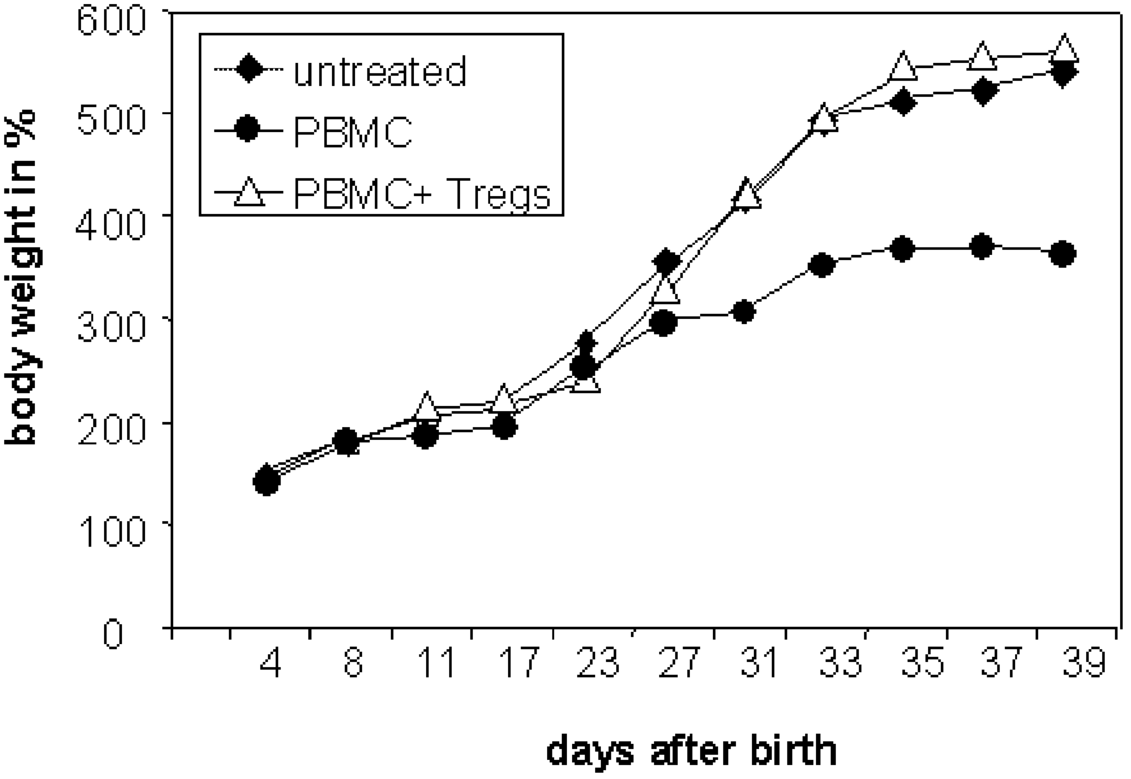

FIG. 3: Induction of GVHD by Transfer of PBMC into NOD-Scid Mice and Prevention of GVHD by Additional Transfer of Regulatory T Cells (Tregs).

Three to six days old NOD-Scid mice are intraperitoneally injected with $1\times10^7$ human PBMC without (circles) or together with $2.5\times10^6$ human regulatory T cells (triangles). Control mice (rhombi) did not receive any PBMC. Mice having received PBMC develop a fatal GVHD, do not grow and die. Animals having additionally received regulatory T cells are protected from development of GVHD and develop normally (3 mice per group). Lack of weight increase/weight loss is used as a parameter to score GVHD severity. The diagram shows the relative body weight at different time points after transfer.

Figure 4:
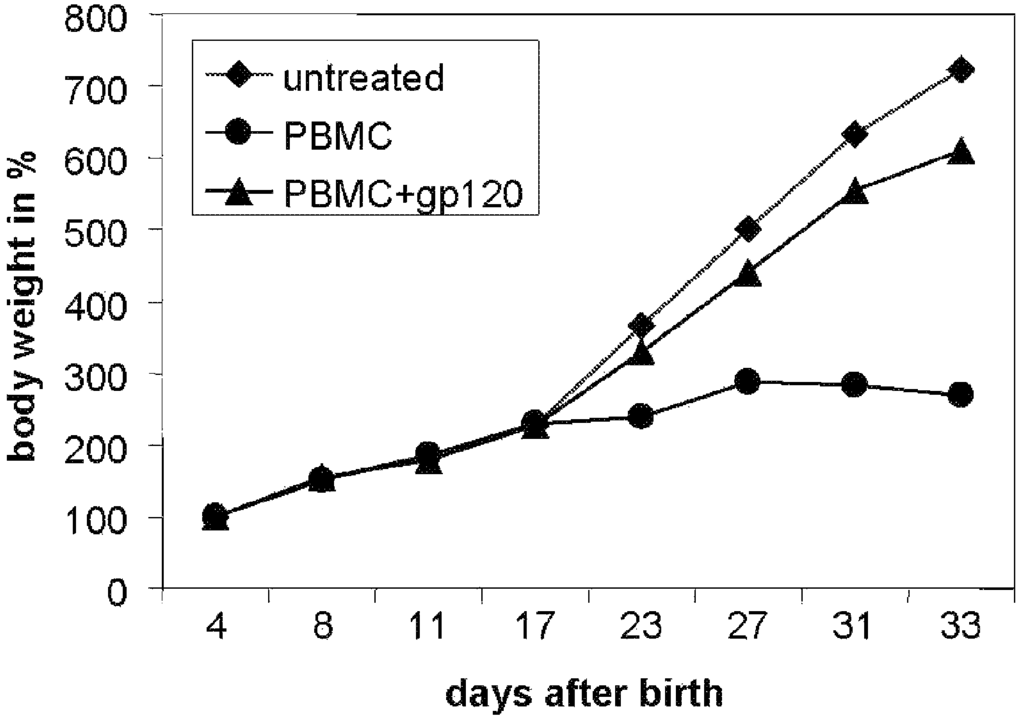

FIG. 4: Induction of GVHD by Transfer of PBMC into Nod-Scid Mice and Prevention of GVHD by Additional Injection of HIV gp120.

Three to six days old NOD-Scid mice are intraperitoneally injected with $1\times10^7$ human PBMC without (circles) or together with 5 μg HIV gp120 (triangles). Control mice (rhombs) did not receive any PBMC. Mice having received PBMC develop a fatal GVHD, do not grow and die. Animals having additionally received HIV gp120 are protected from development of GVHD and develop normally (3 mice per group). Lack of weight increase/weight loss is used as a parameter to score GVHD severity. The diagram shows the relative body weight at different time points after transfer.

Figure 5:
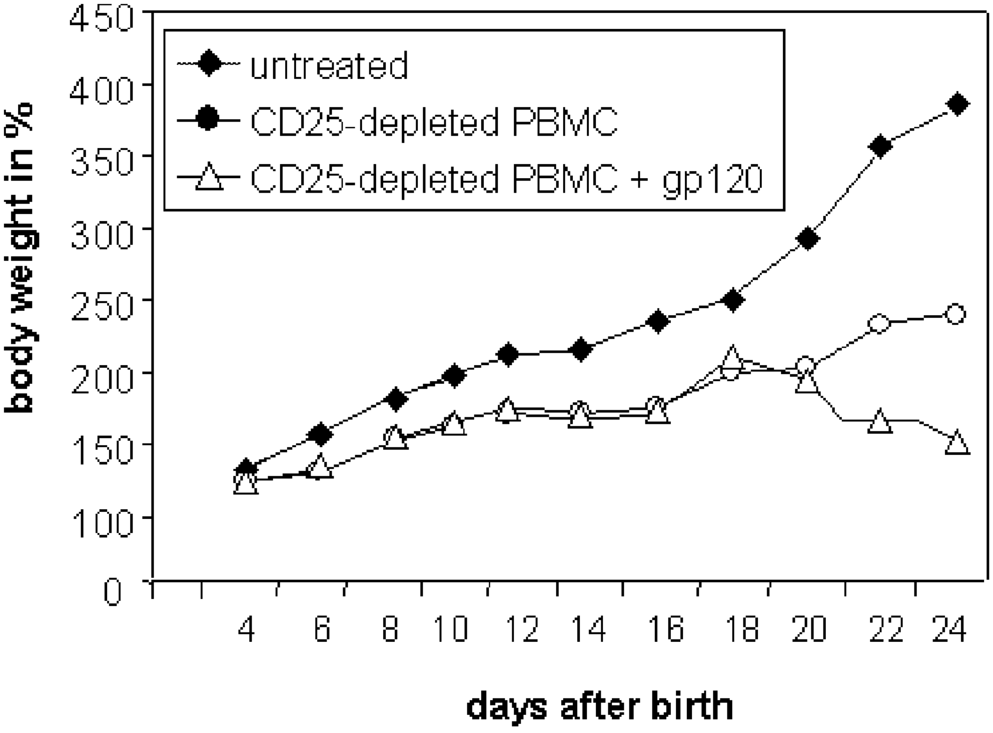

FIG. 5: Prevention of GVHD in Nod-Scid Mice Transferred with PBMC by Additional Injection of HIV gp120 Depends on the Presence of Regulatory T Cells.

Three to six days old NOD-Scid mice are intraperitoneally injected with $1\times10^7$ human CD25-depleted PBMC without (circles) or together with 5 μg HIV gp120 (triangles). Control mice (rhombi) do not receive any PBMC (3 mice per group). Mice having received CD25-depleted PBMC develop a fatal GVHD, do not grow and die. Animals having received $1\times10^7$ human CD25-depleted PBMC and additionally HIV gp120 are not protected from development of GVHD, also do not grow and die. Lack of weight increase/weight loss is used as a parameter to score GVHD severity. The diagram shows the relative body weight at different time points after transfer.

LITERATURE

Arthos J, Deen K C, Chaikin M A, Fornwald J A, Sathe G, Sattentau Q J, Clapham P R, Weiss R A, McDougal J S, Pietropaolo C, et al.

Identification of the residues in human CD4 critical for the binding of HIV. Cell. 1989 57:469-81

Bluestone J A, Tang Q.

Therapeutic vaccination using CD4+CD25+ antigen-specific regulatory T cells. Proc Natl Acad Sci USA. 2004 101 Suppl 2:14622-6

Carrière, D., Vendrell, J. P., Fontaine, C., Reynes, J., Atoui, N., and Pau, B. CD4 $V_1$ domain masking on lymphocytes from HIV-1-infected patients.

In: Leucocyte Typing V: White Cell Differentiation Antigens, Volume 1 pp 475-476, Oxford University Press 1995, Editor: S. F. Schlossman et al.

Castagna A, Biswas P, Beretta A, Lazzarin A.

The appealing story of HIV entry inhibitors: from discovery of biological mechanisms to drug development.

Drugs. 2005 65:879-904

Culp J S, Johansen H, Hellmig B, Beck J, Matthews T J, Delers A, Rosenberg M.

Regulated expression allows high level production and secretion of HIV-1 gp120 envelope glycoprotein in *Drosophila* Schneider cells.

Biotechnology (NY). 1991 9:173-7

Diamond D C, Sleckman B P, Gregory T, Lasky L A, Greenstein J L, Burakoff S J. Inhibition of CD4+ T cell function by the HIV envelope protein, gp120.

J Immunol. 1988 141:3715-7

Fontenot J D, Rudensky A Y.

A well adapted regulatory contrivance: regulatory T cell development and the forkhead family transcription factor Foxp3.

Nat Immunol. 2005 6:331-7

Franke R, Hirsch T, Overwin H, Eichler J.

Synthetic Mimetics of the CD4 Binding Site of HIV-1 gp120 for the Design of Immunogens.

Angew Chem Int Ed Engl. 2007; January 9; [Epub ahead of print]

Hesselton R M, Greiner D L, Mordes J P, Rajan T V, Sullivan J L, Shultz L D.

High levels of human peripheral blood mononuclear cell engraftment and enhanced susceptibility to human immunodeficiency virus type I infection in NOD/LtSz-scid/scid mice.

J Infect Dis. 1995 172: 974-982.

Hoffmann P, Eder R, Kunz-Schughart L A, Andreesen R, Edinger M.

Large-scale in vitro expansion of polyclonal human CD4(+) CD25 high regulatory T cells.

Blood. 2004 104:895-903

Horwitz D A, Zheng S G, Gray J D, Wang J H, Ohtsuka K, Yamagiwa S.

Regulatory T cells generated ex vivo as an approach for the therapy of autoimmune disease.

Semin Immunol. 2004 16:135-43

Hunig T, Dennehy K.

CD28 superagonists: mode of action and therapeutic potential.

Immunol Lett. 2005 100:21-8

Jeffs S A, McKeating J, Lewis S, Craft H, Biram D, Stephens P E, Brady R L.

Antigenicity of truncated forms of the human immunodeficiency virus type 1 envelope glycoprotein.

J Gen Virol. 1996 July; 77 (Pt 7):1403-10

Jameson B A, Rao P E, Kong L I, Hahn B H, Shaw G M, Hood L E, Kent S B.

Location and chemical synthesis of a binding site for HIV-1 on the CD4 protein. Science. 1988 240:1335-9

Kizilisik T A, al-Sebayel M.

Diagnosis and classification of the severity of graft versus host disease after experimental small-bowel transplantation in small animal models.

Transplant Proc. 1997 29:3030-3

Klatzmann D, Champagne E, Chamaret S, Gruest J, Guetard D, Hercend T, Gluckman J C, Montagnier L.

T-lymphocyte T4 molecule behaves as the receptor for human retrovirus LAV.

Nature. 1984 312:767-8

Lasky L A, Groopman J E, Fennie C W, Benz P M, Capon D J, Dowbenko D J, Nakamura G R, Nunes W M, Renz M E, Berman P W.

Neutralization of the AIDS retrovirus by antibodies to a recombinant envelope glycoprotein.

Science. 1986 233:209-12

Leonard C K, Spellman M W, Riddle L, Harris R J, Thomas J N, Gregory T J

Assignment of intrachain disulfide bonds and characterization of potential glycosylation sites of the type 1 recombinant human immunodeficiency virus envelope glycoprotein (gp120) expressed in Chinese hamster ovary cells.

J Biol Chem. 1990 265:10373-82

Lohman K L, Attanasio R, Buck D, Carrillo M A, Allan J S, Kennedy R C.

Characteristics of murine monoclonal anti-CD4. Epitope recognition, idiotype expression, and variable region gene sequence.

J Immunol. 1992 149:3247-53

Markovic I, Clouse K A.

Recent advances in understanding the molecular mechanisms of HIV-1 entry and fusion: revisiting current targets and considering new options for therapeutic intervention.

Curr HIV Res. 2004 2: 223-34

Mizukami T, Fuerst T R, Berger E A, Moss B.

Binding region for human immunodeficiency virus (HIV) and epitopes for HIV-blocking monoclonal antibodies of the CD4 molecule defined by site-directed mutagenesis.

Proc Natl Acad Sci USA. 1988; 85:9273

Moreland L W, Haverty T P, Wacholtz M C, Knowles R W, Bucy R P, Heck L W Jr, Koopman W J.

Nondepleting humanized anti-CD4 monoclonal antibody in patients with refractory rheumatoid arthritis.

J Rheumatol. 1998 25:221-8

Muesing M A, Smith D H, Cabradilla C D, Benton C V, Lasky L A, Capon D J.

Nucleic acid structure and expression of the human AIDS/lymphadenopathy retrovirus.

Nature. 1985 313:450-8

Repke H, Gabuzda D, Palu G, Emmrich F, Sodroski J.

Effects of CD4 synthetic peptides on HIV type I envelope glycoprotein function.

J Immunol. 1992 149:1809-16

Robinson D S.

Regulation: the art of control? Regulatory T cells and asthma and allergy.

Thorax. 2004 59:640-3

Roncarolo, M. G, Bacchetta, R, Bordignon C, Narula, S, Levings, M K

Type 1 T regulatory cells.

Immunol Rev. 2001 182:68-79

Sakaguchi, S.

Naturally arising Foxp3-expressing CD25+CD4+ regulatory T cells in immunological tolerance to self and non-self.

Nature. 2005 6:345-352

Shevach E M.

CD4+CD25+ suppressor T cells: more questions than answers.

Nat Rev Immunol. 2002 2:389-400.

Shultz L D, Schweitzer L, Christianson S W, Gott B, Schweitzer I B, Tennent B, McKenna S, Mobraaten L, Rajan T V, Greiner D L, Leiter E H.

Multiple defects in innate and adaptive immunologic function in NOD/LtSz-scid mice. J Immunol. 1995 154: 180-191.

Starcich B R, Hahn B H, Shaw G M, McNeely P D, Modrow S, Wolf H, Parks E S, Parks W P, Josephs S F, Gallo R C, et al.

Identification and characterization of conserved and variable regions in the envelope gene of HTLV-III/LAV, the retrovirus of AIDS.

Cell. 1986 Jun. 6; 45 (5):637-48

Tang Q, Henriksen K J, Boden E K, Tooley A J, Ye J, Subudhi S K, Zheng X X, Strom T B, Bluestone J A.

Cutting edge: CD28 controls peripheral homeostasis of CD4+CD25+ regulatory T cells.

J Immunol. 2003 171:3348-52

Thornton A M, Shevach E M.

CD4+CD25+ immunoregulatory T cells suppress polyclonal T cell activation in vitro by inhibiting interleukin 2 production.

J Exp Med. 1998 188:287-96

Weiner, H. L.

Induction and mechanism of action of transforming growth factor-beta-secreting Th3 regulatory cells.

Immunol Rev. 2001 182:207-14

Yang Q E, Stephen A G, Adelsberger J W, Roberts P E, Zhu W, Currens M J, Feng Y, Crise B J, Gorelick R J, Rein A R, Fisher R J, Shoemaker R H, Sei S.

Discovery of small-molecule human immunodeficiency virus type 1 entry inhibitors that target the gp120-binding domain of CD4.

J Virol. 2005 79:6122-33

Zheng S G, Wang J H, Gray J D, Soucier H, Horwitz D A.

CD4+ and CD8+ regulatory T cells generated ex vivo with IL-2 and TGF-beta suppress a stimulatory graft-versus-host disease with a lupus-like syndrome. J Immunol. 2004 172:5213-21

The invention claimed is:

1. A method for determining whether a substance can activate a Treg cell via interaction with the HIV-1 gp120-binding site of CD4, comprising:

(a) pre-selecting a substance which can interact with the HIV-1 gp120-binding site of CD4, (b) providing a solution comprising a $CD4^+CD25^+$ Treg cell, (c) adding a pre-selected substance according to (a) under conditions which allow interaction of the substance with a $CD4^+CD25^+$ Treg cell, (d) measuring whether a $CD4^+CD25^+$ Treg cell has been activated, wherein an activated $CD4^+CD25^+$ Treg cell identifies the substance as a Treg cell activator.

2. A method according to claim 1 wherein a Treg cell is a Tr1 cell or a Th3 cell.

3. A method according to claim 1 wherein in (b) of claim 1 a solution is provided which comprises (i) a $CD4^+CD25^+$ Treg cell, (ii) an inactivated syngenic CD3-depleted PBMC (peripheral blood mononuclear cell) or a dendritic cell (DC) and (iii) an allogeneic $CD8^+$ T cell or an allogeneic $CD4^+$ T cell.

4. A method according to claim 3 wherein the inactivated syngenic CD3-depleted PBMC has been inactivated via irradiation or via mitomycin C.

5. A method according to claim 3 wherein the measuring of whether a $CD4^+CD25^+$ Treg cell has been activated is determined by measuring whether a $CD8^+$ T cell has been suppressed, wherein a suppressed $CD8^+$ T cell identifies an activated $CD4^+CD25^+$Treg cell and therewith identifies the substance as a Treg cell activator.

6. A method according to claim 5 wherein measuring whether a $CD8^+$ T cell has been suppressed is determined by measuring inhibited proliferation of the $CD8^+$ T cell or by measuring reduced CD25 expression of the $CD8^+$ T cell.

7. A method according to claim 5 wherein measuring whether a $CD8^+$ T cell has been suppressed is determined by measuring inhibited cytokine production of the $CD8^+$ T cell.

8. A method according to claim 7 wherein the cytokine is IFNγ or IL2 or TNF-α.

9. A method according to claim 3 wherein the measuring of whether a $CD4^+CD25^+$ Treg cell has been activated is determined by measuring whether a $CD4^+$ T cell has been suppressed, wherein a suppressed $CD4^+$ T cell identifies an activated $CD4^+CD25^+$ Treg cell and therewith identifies the substance as a Treg cell activator.

10. A method according to claim 9 wherein measuring whether a $CD4^+$ T cell has been suppressed is determined by measuring inhibited proliferation of the $CD4^+$ T cell or by measuring reduced CD25 expression of the $CD4^+$ T cell.

11. A method according to claim 9 wherein measuring whether a $CD4^+$ T cell has been suppressed is determined by measuring inhibited cytokine production of the $CD4^+$ T cell.

12. A method according to claim 11 wherein the cytokine is IFNγ or IL2 or TNF-α.

13. A method according to claim 1 wherein in (d) of claim 16 the measuring whether a $CD4^+CD25^+$ Treg cell has been activated is determined by measuring the amount of intracellular cAMP and wherein an increased amount of intracellular cAMP is indicative for an activated $CD4^+CD25^+$ Treg cell and therewith identifies the substance as a Treg cell activator.

14. A method according to claim 1 wherein step (a) of claim 16 comprises:

(a) providing a first solution comprising CD4, (b) providing a second solution comprising CD4, (c) adding to the first solution a substance to be tested and HIV-1 gp120 under conditions which allow binding of HIV-1 gp120 with CD4, (d) adding to the second solution HIV-1 gp120 under conditions like (c) allowing binding of HIV-1 gp120 with CD4, (e) measuring in the first and in the second solution whether the HIV-1 gp120 has bound to the CD4 wherein a reduced amount of bound HIV-1 gp120 in the first solution indicates that the substance can interact with HIV-1 gp120-binding site of CD4.

15. A method according to claim 14 wherein instead of CD4 a peptide is used which comprises the amino acid stretch as set forth in SEQ ID NO.1.

16. A method according to claim 15 wherein instead of CD4 a peptide is used as set forth in SEQ ID NO.1.

17. A method according to claim 14 wherein instead of HIV-1 gp120 a peptide is used selected from a group consisting of a peptide comprising the amino acid sequence as set forth in SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, and SEQ ID NO.: 10.

18. A method according to claim 14 wherein instead of HIV-1 gp120 a peptide is used selected from a group consisting of a peptide consisting of the amino acid sequence as set forth in SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, and SEQ ID NO.: 10.

19. A method for determining whether a substance can activate a regulatory T cell (Treg) via interaction with the epitope as set forth in SEQ ID NO: 1 comprising:

(a) providing a first solution comprising a $CD4^+CD25^+$ Treg cell, (b) adding a substance to be tested under conditions which allow interaction of the substance with a $CD4^+CD25^+$ Treg cell, (c) measuring whether a $CD4^+CD25^+$ Treg cell of the first solution has been activated, (d) providing a second solution comprising a $CD4^+CD25^+$ Treg cell, (e) adding the substance to be tested and a peptide comprising an amino acid sequence as set forth in SEQ ID NO: 1 under conditions like (b), (f) measuring whether a $CD4^+CD25^+$ Treg cell of the second solution has been activated, (g) comparing results obtained from (c) with those obtained from (f) wherein a reduced activation of (f) identifies the substance as a Treg cell activator which activates a $CD4^+$ $CD25^+$ Treg cell via interaction with the epitope as set forth in SEQ ID NO: 1.

20. A method according to claim 19 wherein in step (e) of claim 34 the peptide used is selected from a group consisting of an isolated peptide spanning amino acid No. 1-31 of SEQ ID NO 1, No. 26 to 458 of SEQ ID NO.: 2, No. 26 to 419 of SEQ ID NO.:2, No. 26 to 207 of SEQ ID NO.: 2, No. 26 to 131 of SEQ ID NO.: 2 and No. 46 to 89 of SEQ ID NO.: 2.

21. A method according to claim 19 wherein in step (e) of claim 34 the peptide used is an isolated peptide spanning amino acid No. 1 to 31 of SEQ ID NO.: 1 and having additional up-stream and/or downstream amino acids with the prerequisite that the additional amino acids do not hinder binding of a substance to the amino acid stretch as set forth in SEQ ID No.: 1.

22. A method according to claim 21 wherein the additional up-stream amino acid or amino acid stretch is selected from a group consisting of the amino acid or amino acid stretch as set forth in SEQ ID NO.: 2 at position 53, at position 52-53, at position 51-53, at position 50-53, at position 49-53, at position 48-53, at position 47-53, at position 46-53, at position 45-53, at position 44-53, at position 43-53, at position 42-53, at position 41-53, at position 40-53, at position 39-53, at position 38-53, at position 37-53, at position 36-53, at position 35-53, at position 34-53, at position 33-53, at position 32-53, at position 31-53, at position 30-53, at position 29-53, at position 28-53, at position 27-53, at position 26-53, at position 25-53, at position 24-53, at position 23-53, at position 22-53, at position 21-53, at position 20-53, at position 19-53, at position 18-53, at position 17-53, at position 16-53, at position 15-53, at position 14-53, at position 13-53, at position 12-53, at position 11-53, at position 10-53, at position 9-53, at position 8-53, at position 7-53, at position 6-53, at position 5-53, at position 4-53, at position 3-53, at position 2-53, and at position 1-53.

23. A method according to claim 21 wherein additional downstream amino acids are given in SEQ ID NO.: 2 at position 85, or at position 85 to n, wherein n is an integer between 86-458.

24. A method according to claim 19 wherein a Treg cell is a Tr1 cell or a Th3 cell.

25. A method according to claim 19 wherein in (a) and (d) of claim 19 a solution is provided which comprises (i) a $CD4^+CD25^+$ Treg cell, (ii) an inactivated syngenic CD3-depleted PBMC (peripheral blood mononuclear cell) or a dendritic cell (DC) and (iii) an allogeneic $CD8^+$ T cell or an allogeneic $CD4^+$ T cell.

26. A method according to claim 25 wherein the inactivated syngenic CD3-depleted PBMC has been inactivated via irradiation or via mitomycin C.

27. A method according to claim 25 the measuring of whether a $CD4^+CD25^+$ Treg cell has been activated is determined by measuring whether a $CD8^+$ T cell has been suppressed, wherein a suppressed $CD8^+$ T cell identifies an activated $CD4^+CD25^+$ Treg cell and therewith identifies the substance as a Treg cell activator.

28. A method according to claim 27 wherein measuring whether a $CD8^+$ T cell has been suppressed is determined by measuring inhibited proliferation of the $CD8^+$ T cell or by measuring reduced CD25 expression of the $CD8^+$ T cell.

29. A method according to claim 27 wherein measuring whether a $CD8^+$ T cell has been suppressed is determined by measuring inhibited cytokine production of the $CD8^+$ T cell.

30. A method according to claim 29 wherein the cytokine is IFN$\gamma$ or IL2 or TNF-$\alpha$.

31. A method according to claim 25 wherein the measuring of whether a Treg cell has been activated is determined by measuring whether a $CD4^+$ T cell has been suppressed, wherein a suppressed $CD4^+$ T cell identifies an activated $CD4^+CD25^+$ Treg cell and therewith identifies the substance as a Treg cell activator.

32. A method according to claim 31 wherein measuring whether a $CD4^+$ T cell has been suppressed is determined by measuring inhibited proliferation of the $CD4^+$ T cell or by measuring reduced CD25 expression of the $CD4^+$ T cell.

33. A method according to claim 31 wherein measuring whether a $CD4^+$ T cell has been suppressed is determined by measuring inhibited cytokine production of the $CD4^+$ T cell.

34. A method according to claim 33 wherein the cytokine is IFN$\gamma$ or IL2 or TNF-$\alpha$.

35. A method according to claim 19 wherein the measuring of whether a Treg cell has been activated is determined by measuring the amount of intracellular cAMP and wherein an increased amount of intracellular cAMP is indicative for an activated Treg cell and therewith identifies the substance as a Treg cell activator.

* * * * *